(12) United States Patent
Dakka et al.

(10) Patent No.: US 9,815,767 B2
(45) Date of Patent: *Nov. 14, 2017

(54) ALKYL AROMATIC HYDROALKYLATION FOR THE PRODUCTION OF PLASTICIZERS

(71) Applicant: ExxonMobil Chemical Patents Inc., Baytown, TX (US)

(72) Inventors: Jihad M. Dakka, Whitehouse Station, NJ (US); Lorenzo C. DeCaul, Langhorne, PA (US); Christine A. Costello, Easton, PA (US); Edmund J. Mozeleski, Somerset, NJ (US); Pierre Osterrieth, Brussels (BE); Stephen Zushma, Clinton, NJ (US); Allen D. Godwin, Brenham, TX (US); Diana Smimova, Spring, TX (US); Catherine A. Faler, Houston, TX (US); Victor DeFlorio, Cranford, NJ (US); Didier A. Naert, Brussels (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,055

(22) Filed: Apr. 25, 2016

(65) Prior Publication Data
US 2016/0237022 A1    Aug. 18, 2016

Related U.S. Application Data

(60) Continuation of application No. 14/516,239, filed on Oct. 16, 2014, now Pat. No. 9,321,898, which is a
(Continued)

(51) Int. Cl.
| | | |
|---|---|---|
| C08K 5/00 | (2006.01) |
| C07C 69/76 | (2006.01) |
| C08K 5/101 | (2006.01) |
| C08K 5/12 | (2006.01) |
| C09D 127/06 | (2006.01) |
| H01B 3/44 | (2006.01) |
| C08J 5/18 | (2006.01) |
| C08K 5/10 | (2006.01) |
| D21H 27/20 | (2006.01) |
| C07C 67/08 | (2006.01) |
| C07C 67/39 | (2006.01) |
| C07C 69/78 | (2006.01) |
| C08K 3/10 | (2006.01) |
| C08K 5/103 | (2006.01) |
| D06N 7/00 | (2006.01) |
| D06M 13/224 | (2006.01) |
| D06N 3/00 | (2006.01) |
| D06N 5/00 | (2006.01) |
| C07C 2/68 | (2006.01) |

(Continued)

(52) U.S. Cl.
CPC ............... *C07C 69/76* (2013.01); *C07C 2/68* (2013.01); *C07C 2/76* (2013.01); *C07C 51/285* (2013.01); *C07C 67/08* (2013.01); *C07C 67/39* (2013.01); *C07C 69/78* (2013.01); *C08J 5/18* (2013.01); *C08K 3/10* (2013.01); *C08K 5/10* (2013.01); *C08K 5/101* (2013.01); *C08K 5/103* (2013.01); *C08K 5/12* (2013.01); *C09D 127/06* (2013.01); *D06M 13/224* (2013.01); *D06N 3/0059* (2013.01); *D06N 5/00* (2013.01); *D06N 7/0002* (2013.01); *D21H 27/20* (2013.01); *H01B 3/443* (2013.01); *C07C 2601/14* (2017.05); *C08J 2327/06* (2013.01); *C08K 2201/014* (2013.01); *Y10T 428/2964* (2015.01); *Y10T 428/31935* (2015.04)

(58) Field of Classification Search
CPC ....... C07C 69/76; C07C 67/08; C07C 51/285; C07C 2/76; C07C 2/68; C07C 2101/14; C08K 5/103
USPC ........................................................ 524/287
See application file for complete search history.

(56) References Cited

U.S. PATENT DOCUMENTS

| | | |
|---|---|---|
| 2,520,084 A | 8/1950 | Dazzi et al. |
| 2,634,248 A | 4/1953 | Dazzi |

(Continued)

FOREIGN PATENT DOCUMENTS

| | | |
|---|---|---|
| JP | 2003/246755 | 9/2003 |
| WO | WO 97/49654 | 12/1997 |

(Continued)

OTHER PUBLICATIONS

Dikusar et al., Russian Journal of General Chemistry, 74, 8, 1259-1263, 2004.*

(Continued)

*Primary Examiner* — Hui Chin

(57) ABSTRACT

Provided are compounds of the following:

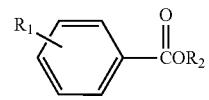

wherein $R_1$ is a saturated or unsaturated cyclic hydrocarbon optionally substituted with an alkyl and/or an OXO-ester, and $R_2$ is a $C_4$ to $C_{14}$ hydrocarbyl, preferably the residue of a $C_4$ to $C_{14}$ OXO-alcohol. Also provided are processes for making the compounds and plasticized polymer compositions containing said compounds.

7 Claims, 2 Drawing Sheets

Related U.S. Application Data division of application No. 14/164,889, filed on Jan. 27, 2014, now Pat. No. 9,085,669, which is a continuation-in-part of application No. 13/751,835, filed on Jan. 28, 2013, now Pat. No. 8,829,093.

(51) Int. Cl.
*C07C 2/76* (2006.01)
*C07C 51/285* (2006.01)

(56) References Cited

U.S. PATENT DOCUMENTS

| | | | |
|---|---|---|---|
| 2,786,076 | A | 3/1957 | O'Connor et al. |
| 3,950,434 | A | 4/1976 | Kominami et al. |
| 3,962,362 | A | 6/1976 | Suggitt |
| 5,188,815 | A * | 2/1993 | Coates ............ G01K 11/165 252/299.01 |
| 6,355,711 | B1 | 3/2002 | Godwin et al. |
| 7,579,511 | B1 | 8/2009 | Dakka et al. |
| 8,829,093 | B2 | 9/2014 | Dakka et al. |
| 2009/0299111 | A1 | 12/2009 | Kanbara et al. |
| 2011/0184105 | A1 | 7/2011 | Dakka et al. |
| 2012/0283494 | A1 | 11/2012 | Smith et al. |
| 2014/0058143 | A1 | 2/2014 | Yamamoto et al. |
| 2014/0212666 | A1 | 7/2014 | Dakka et al. |
| 2014/0272626 | A1 | 9/2014 | Berlowitz et al. |
| 2014/0275605 | A1 | 9/2014 | Dakka et al. |
| 2014/0275606 | A1 | 9/2014 | Bai et al. |
| 2014/0275607 | A1 | 9/2014 | Dakka et al. |
| 2014/0275609 | A1 | 9/2014 | Dakka et al. |
| 2014/0315021 | A1 | 10/2014 | Naert et al. |
| 2014/0316155 | A1 | 10/2014 | Dakka et al. |
| 2014/0378697 | A1 | 12/2014 | de Smit et al. |
| 2015/0080545 | A1 | 3/2015 | Dakka et al. |
| 2015/0080546 | A1 | 3/2015 | Dakka et al. |

FOREIGN PATENT DOCUMENTS

| | | |
|---|---|---|
| WO | WO 2014/117076 | 7/2014 |
| WO | WO 2014/159094 | 10/2014 |
| WO | WO 2014/159106 | 10/2014 |

OTHER PUBLICATIONS

Inoue et al., Tetrahedron, 56, 9601-9605, 2000.*
Shen et al., Polymer Preprints, ACS Division of Polymer Chemistry, 45(1), 518-519, 2004.*
Brenda et al., Synlett, (11), 809-810, 1991.*
U.S. Appl. No. 62/012,024, filed Jun. 13, 2014, Salciccioli et al.
U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.
U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 14/516,239, filed Oct. 16, 2014, Dakka et al.
Brechtelsbaur, C. et al., "Shape selective methylation of biphenyl within zeolites: An example of transition state selectivity," Applied Catalysis A: General, vol. 161, 1997, pp. 79-92.
Hill, Roberta B. et al., "Esters and Amides of 2,2'-Diphenic Acid," Department of Chemistry, Tenessee Polytechnic Institute, Cokeville, TN, vol. 8(2), Apr. 1963, pp. 233-234.
Kamiyama, T. et al., "Hydroalkylation of benzenes with Pd—Al2O3 and NaCl—AlCl3," Chemistry Letters, 1979, pp. 261-264.
Krigbaum et al., "Aromatic Polyesters Forming Thermotropic Smectic Mesophases," Journal of Polymer Science: Polymer Letters Edition, vol. 20, 1982, pp. 109-115.
Lagidze et al., "Analysis of Substances Produced BY Reaction Between Aluminum Chloride and Diphenyl In Dearomatized Ligroin," V.I. Leni-n Georgian Polytechnic Institute (1968), No. 2 (122), pp. 36-44 (English Translation).
Ryabov, A.D. et al., "Palladium (II)-Catalyzed Oxidation of Substituted Benzenes to Biaryls by Tris(Trifluoroacetato)Thallium(III)," Tetrahedron Letters, vol. 22, No. 38, 1981, pp. 3793-3796.
Shen, Jian-Ping et al., "Shape-selective sysnthesis of 4.4'dimethylbiphenyl. 1. Methylation of 4-methylbiphenyl over modified zeolite catalysts," Catalysis Letters, vol. 65, 2000, pp. 147-151.
Sing, P.K. et. al, "*Studies on Isomer Distribution in the Products Obtained by Friedelcrafts Alkylation of Toluene with Cyclic Electrophiles*," Nat'l Academy Science Letters, 1983, vol. 6(10), pp. 321-325.

* cited by examiner

ALKYL AROMATIC HYDROALKYLATION FOR THE PRODUCTION OF PLASTICIZERS

PRIORITY

This application is a continuation of U.S. Ser. No. 14/516,239, filed Oct. 16, 2014, which is a divisional of U.S. Ser. No. 14/164,889, filed Jan. 27, 2014, which is a continuation-in-part of U.S. application Ser. No. 13/751,835, filed Jan. 28, 2013, the disclosures of which are incorporated herein by reference in their entireties.

FIELD

This disclosure relates to a route to non-phthalate, aromatic ester plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not been found.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Provisional Patent Application No. 61/040,480, filed Mar. 28, 2008) or polyketones, such as described in U.S. Pat. No. 6,777,514; and also co-pending, commonly-assigned, U.S. Patent Publication No. 2008/0242895, filed Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Copending and commonly assigned U.S. Provisional Patent Application No. 61/203,626, filed Dec. 24, 2008, discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins.

U.S. Pat. No. 2,520,084 to Dazzi discloses plasticized vinyl chloride polymers using esters of phenyl benzoic acids and aliphatic hydrocarbon alcohols as plasticizers. Suitable esters are 2-ethylhexyl m-phenylbenzoate, the corresponding para- and ortho-phenylbenzoates, or mixtures thereof, and the various phenylbenzoates of n-hexyl, 2-methylheptyl, dodecyl, dimethylheptyl, 2-butoxyethyl, and isooctyl alcohols, and other homologous straight and branched alcohols having 8 to 14 atoms. The butoxyethyl and 2-ethylhexyl esters of phenylbenzoic acid are exemplified.

"Esters of diphenic acid and their plasticizing properties", Kulev et al., *Izvestiya Tomskogo Politekhnicheskogo Instituta* (1961) 111, discloses diisoamyl diphenate, bis (2-ethylhexyl) diphenate and mixed heptyl, octyl and nonyl diphenates, prepared by esterification of diphenic acid, useful as plasticizers for vinyl chloride.

"Synthesis of dialkyl diphenates and their properties", Shioda et al., *Yuki Gosei Kagaku Kvokaishi* (1959), 17, discloses dialkyl diphenates of $C_1$ to $C_8$ alcohols, useful as plasticizers for poly(vinyl chloride) formed by converting diphenic acid to diphenic anhydride and esterifying the diphenic anhydride, necessarily resulting in 2,2'-substituted diesters of diphenic anhydride.

Other references of interest include: Clary, International Journal of Organic Chemistry, 2013, 3, 143-147; U.S. 2012/0108874 A1; and U.S. Pat. No. 5,138,022.

Thus, what is needed is a method of making a general purpose plasticizer having suitable melting or chemical and thermal stability, pour point, glass transition, increased compatibility, good performance and low temperature properties.

SUMMARY

In one aspect, the present application provides compounds of the formula:

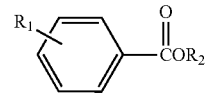

wherein $R_1$ is a saturated or unsaturated cyclic hydrocarbon optionally substituted with an alkyl and/or an OXO-ester, and $R_2$ is a $C_4$ to $C_{14}$ hydrocarbyl, preferably a hydrocarbon residue of a $C_4$ to $C_{14}$ OXO-alcohol.

In one aspect, the present application provides for mixtures comprising two or more compounds of the formula:

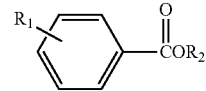

wherein R₁ is a saturated or unsaturated cyclic hydrocarbon optionally substituted with an alkyl and/or an OXO-ester, and R₂ is a C₄ to C₁₄ hydrocarbyl, preferably a hydrocarbon residue of a C₄ to C₁₄ OXO-alcohol. In a preferred embodiment of the invention, the mixture comprises two or more compounds of the formula above where the R₂ groups are different. In a preferred embodiment of the invention, the mixture comprises two or more compounds of the formula above where the R₂ groups are the same.

In another aspect, the present application provides a process for making compounds of the formula:

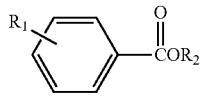

wherein R₁ is a cyclic hydrocarbon optionally substituted with an alkyl and/or an OXO-ester, and R₂ is a C₄ to C₁₄ hydrocarbyl, preferably a hydrocarbon residue of a C₄ to C₁₄ OXO-alcohol, comprising the steps of: reacting benzene or alkylated benzene under conditions appropriate to form alkylated biphenyl; optionally alkylating biphenyl to form said alkylated biphenyl; oxidizing the alkyl group(s) on said alkylated biphenyl to form at least one acid group; and reacting said acid group(s) with an OXO-alcohol under esterification conditions to form said compounds.

In another aspect, the present application provides a polymer composition comprising a thermoplastic polymer and at least one plasticizer of the formula:

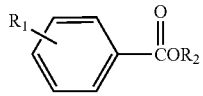

wherein R₁ is a saturated and unsaturated cyclic hydrocarbon optionally substituted with an alkyl and/or an OXO-ester, and R₂ is a C₄ to C₁₄ hydrocarbyl, preferably a hydrocarbon residue of a C₄ to C₁₄ OXO-alcohol.

DETAILED DESCRIPTION

Figure 1:
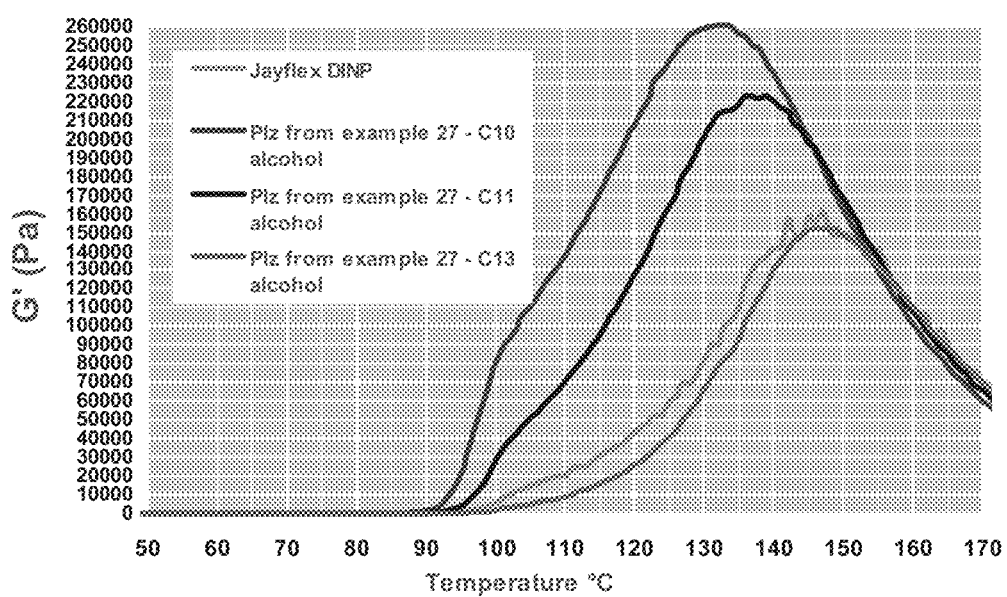
FIG. 1 is a graph of dynamic mechanical analysis of the plastisols of Example 28.

All numerical values within the detailed description and the claims herein are modified by "about" or "approximately" the indicated value, and take into account experimental error and variations that would be expected by a person having ordinary skill in the art.

Unless otherwise indicated, room temperature is about 21° C.

There is an increased interest in developing new plasticizers that offer alternatives to phthalates and which possess good plasticizer performance characteristics but are still competitive economically. The present disclosure is directed towards non-phthalate, mono- or diester plasticizers, particularly OXO-ester plasticizers, that can be made from low cost feeds and employ fewer manufacturing steps in order to meet economic targets.

It has been determined that compounds of the general formula:

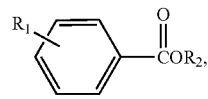

wherein R₁ is a saturated or unsaturated cyclic hydrocarbon, optionally substituted with an alkyl and/or an OXO-ester, and R₂ is a C₄ to C₁₄ hydrocarbyl, preferably the residue of a C₄ to C₁₄ OXO-alcohol, are particularly useful as replacements for general purpose phthalate plasticizers like bis(2-ethylhexyl) phthalate (DEHP) or di-isononylphthalate (DINP) or di-isodecyl phthalate (DIDP) or di-2-propylheptyl phthalate (DPHP), which are the largest volume plasticizers used in conventional polymer plastics. In any embodiment of the invention described herein, R₁ is an aromatic ring, preferably a substituted aromatic ring, preferably a C₆ aromatic ring, preferably a substituted C₆ aromatic ring, preferably an alkyl substituted C₆ aromatic ring, preferably a methyl substituted C₆ aromatic ring.

In one aspect, the present application provides for mixtures comprising two or more (alternately three, four, five, six, or more) compounds of the formula:

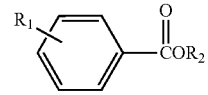

wherein R₁ is a saturated or unsaturated cyclic hydrocarbon optionally substituted with an alkyl and/or an OXO-ester, and R₂ is a C₄ to C₁₄ hydrocarbyl, preferably a hydrocarbon residue of a C₄ to C₁₄ OXO-alcohol. In a preferred embodiment of the invention the mixture comprises one or more compounds where R₁ is saturated, and one or more compounds where R₁ is unsaturated. Alternately, in another preferred embodiment of the invention, the mixture comprises: 1) one or more compounds where R₁ is a saturated C₆ ring optionally substituted with an alkyl and/or an OXO-ester, and 2) one or more compounds where R₁ is an unsaturated C₆ ring optionally substituted with an alkyl and/or an OXO-ester.

In any embodiment of the invention described herein R₁ may be located at the ortho-, meta- or para-position. In any embodiment of the invention described herein R₁ may be phenyl located at the para-position. In any embodiment of the invention described herein R₁ may be an alkyl and/or an OXO-ester-substituted phenyl at the ortho-, meta-, or para-position, preferably R₁ is an alkyl and/or an OXO-ester-substituted cyclohexyl at the ortho-, meta-, or para-position, such as phenyl, methyl phenyl, benzyl, and the like. In any embodiment of the invention described herein R₁ may be a substituted phenyl located at the ortho-, meta- or para-position. In any embodiment of the invention described herein R₁ may be phenyl located at the para-position, preferably a substituted phenyl. In any embodiment of the invention described herein R₁ may be phenyl located at the para-position, preferably a substituted phenyl, where the phenyl is substituted with a C₁ to C₂₀ alkyl, preferably a C₁ to C₄ alkyl, preferably a C₁ alkyl at the ortho-, meta- or para-position, for example R¹ may be tolyl. The phenyl group may be substituted at the 1, 2, 3, 4 or 5 positions, preferably at one position with a C₁ to C₂₀ alkyl, such as methyl, ethyl, propyl, butyl, pentyl, hexyl, heptyl, octyl, nonyl, decyl, undecyl, dodecyl, and isomers thereof.

In any embodiment of the invention described herein, $R_2$ may be a $C_4$ to $C_{14}$ hydrocarbyl, preferably a $C_5$ to $C_{14}$ hydrocarbyl, such as butyl, pentyl, hexyl, heptyl, octyl, nonyl, decyl, undecyl, dodecyl, tridecyl, tetradecyl and an isomer thereof, preferably $C_5$, $C_6$, $C_9$ and $C_{10}$ hydrocarbyl, preferably a $C_5$ to $C_{11}$, preferably $C_6$ to $C_{10}$ hydrocarbyl.

In another embodiment of the invention, $R_1$ is substituted with an

group, where $R_3$ is a $C_4$ to $C_{14}$ hydrocarbyl, preferably a hydrocarbon residue of a $C_4$ to $C_{14}$ OXO-alcohol, preferably a $C_5$ to $C_{10}$ hydrocarbyl, such as butyl, pentyl, hexyl, heptyl, octyl, nonyl, decyl, undecyl, dodecyl, tridecyl, tetradecyl or an isomer thereof, preferably a $C_5$, $C_6$, $C_9$ or $C_{10}$ hydrocarbyl. In any embodiment of the invention, $R_1$ may be the same as the

group of the general formula:

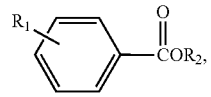

wherein $R_1$ is a saturated or unsaturated cyclic hydrocarbon, optionally substituted with an alkyl and/or an OXO-ester, and $R_2$ is a $C_4$ to $C_{14}$ hydrocarbyl, preferably the residue of a $C_4$ to $C_{14}$ OXO-alcohol.

In any embodiment of the invention described herein $R_2$ may be the hydrocarbon residue of a $C_5$ to $C_{10}$ OXO-alcohol averaging from 0.2 to 5.0 branches per residue.

In any embodiment of the invention described herein the hydrocarbon residue averages from 0.05 to 0.4 branches per residue at the alcoholic beta carbon.

In any embodiment of the invention described herein the hydrocarbon residue averages at least 1.3 to 5.0 methyl branches per residue.

In any embodiment of the invention described herein the hydrocarbon residue averages from 0.35 to 1.5 pendant methyl branches per residue.

In a preferred embodiment of the invention, the compounds produced herein are represented by the formula:

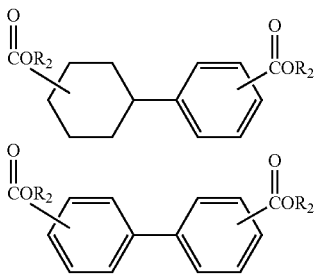

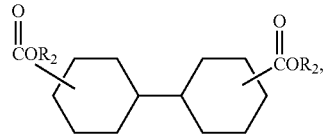

where each $R_2$ is, independently, a $C_4$ to $C_{14}$ hydrocarbyl, preferably the residue of a $C_4$ to $C_{14}$ OXO-alcohol, preferably each $R_2$ is, independently, a $C_6$ to $C_9$ hydrocarbyl, preferably a $C_6$, $C_7$, $C_8$ or $C_9$ hydrocarbyl, preferably a $C_6$, $C_7$, $C_8$ or $C_9$ alkyl, such as hexyl, heptyl, octyl or nonyl, or an isomer thereof.

In a preferred embodiment of the invention, the compounds produced herein are represented by the formula:

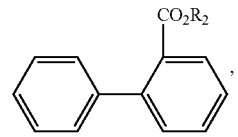

wherein $R^2$=a $C_5$ to $C_{14}$ hydrocarbyl, preferably $R_2$ is $C_9H_{19}$, $C_{10}H_{21}$ or $C_{13}H_{27}$.

In a preferred embodiment of the invention, the compounds produced herein are represented by the formula:

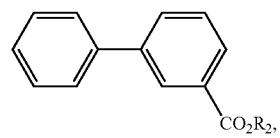

wherein $R^2$=a $C_5$ to $C_{14}$ hydrocarbyl, preferably $R_2$ is $C_9H_{19}$, $C_{10}H_{21}$, or $C_{13}H_{27}$.

In a preferred embodiment of the invention, the compounds produced herein may be a mixture of the following at any ratio:

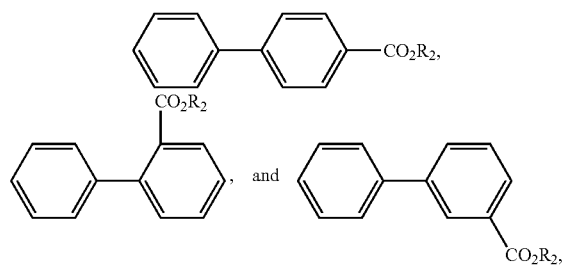

wherein $R^2$=a $C_5$ to $C_{14}$ hydrocarbyl, preferably $R_2$ is $C_9H_{19}$, $C_{10}H_{21}$, or $C_{13}H_{27}$.

In a preferred embodiment of the invention, the compounds produced herein are represented by the formulas:

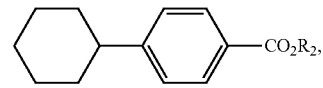

-continued

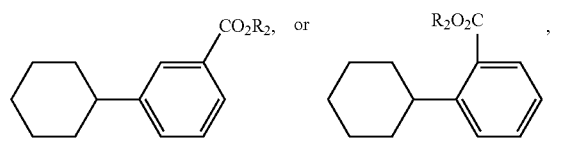

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formulas:

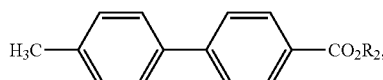

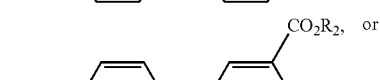

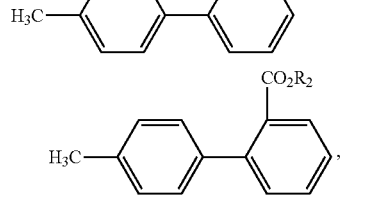

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formula (or comprise a mixture of compounds represented by the formulas):

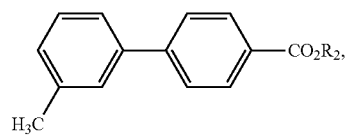

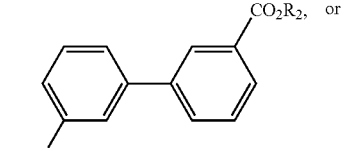

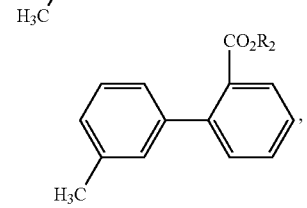

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formula (or comprise a mixture of compounds represented by the formulas):

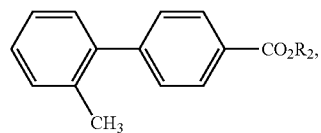

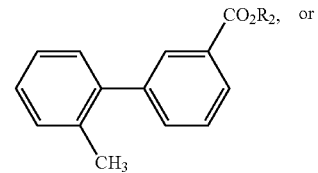

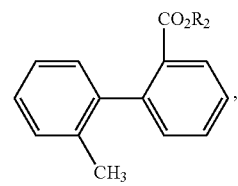

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formula (or comprise a mixture of compounds represented by the formulas):

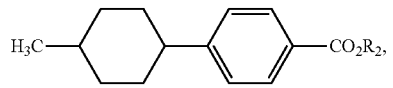

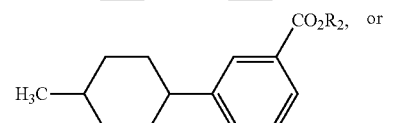

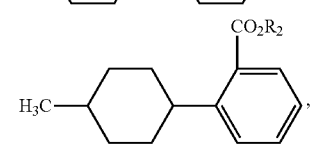

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formula (or comprise a mixture of compounds represented by the formulas):

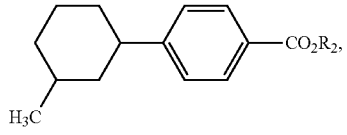

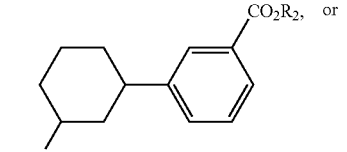

-continued

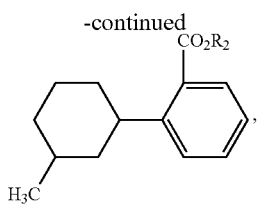

wherein $R^2$=a $C_5$ to $C_{14}$ hydrocarbyl, preferably $R_2$=$C_9H_{19}$, $C_{10}H_{21}$, or $C_{13}H_{27}$.

In a preferred embodiment of the invention, the compounds produced herein are represented by the formula (or comprise a mixture of compounds represented by the formulas):

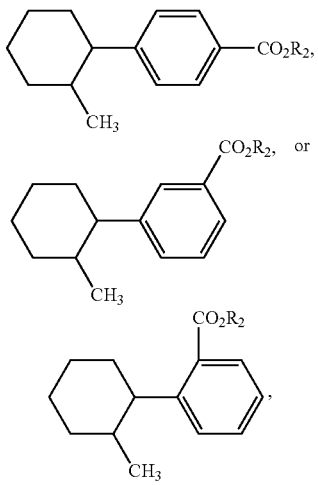

wherein $R^2$=a $C_5$ to $C_{14}$ hydrocarbyl, preferably $R_2$=$C_9H_{19}$, $C_{10}H_{21}$, or $C_{13}H_{27}$.

Additionally, compositions described by of the formulas depicted herein may be partially or fully hydrogenated, such that the final composition may contain compounds represented by the formula:

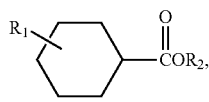

wherein $R_1$ is a saturated or unsaturated cyclic hydrocarbon, optionally substituted with an alkyl and/or an OXO-ester, and $R_2$ is a $C_4$ to $C_{14}$ hydrocarbyl, preferably the residue of a $C_4$ to $C_{14}$ OXO-alcohol, for example:

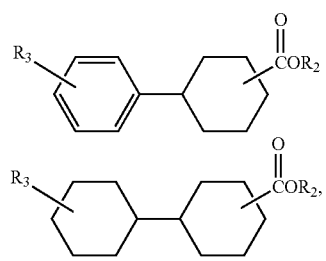

wherein $R_3$ is an alkyl and/or an OXO-ester (such as methyl or —$CO_2R_2$*), $R_2$ is a $C_4$ to $C_{14}$ hydrocarbyl, preferably the residue of a $C_4$ to $C_{14}$ OXO-alcohol, $R_2$* is a $C_4$ to $C_{14}$ hydrocarbyl, preferably the residue of a $C_4$ to $C_{14}$ OXO-alcohol, that may be the same or different as $R_2$.

In a preferred embodiment of the invention, the compound is represented by the formulas:

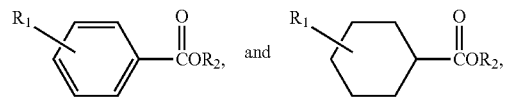

wherein each $R_1$ is, independently, a saturated or unsaturated cyclic hydrocarbon, optionally substituted with an alkyl and/or an OXO-ester, and each $R_2$ is, independently, a $C_4$ to $C_{14}$ hydrocarbyl, preferably the residue of a $C_4$ to $C_{14}$ OXO-alcohol, preferably the compound is a mixture of compounds represented by the formulas:

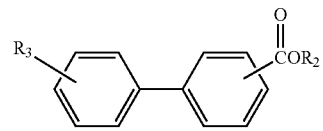

and one or more of

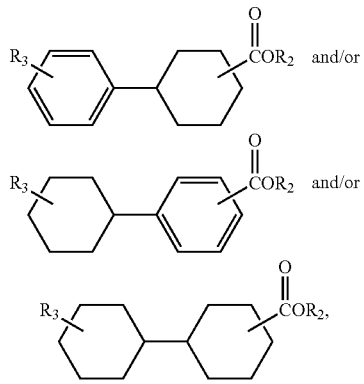

wherein each $R_3$ is, independently, an alkyl and/or an OXO-ester (such as methyl or —$CO_2R_2$*), $R_2$ is a $C_4$ to $C_{14}$ hydrocarbyl, preferably the residue of a $C_4$ to $C_{14}$ OXO-alcohol, $R_2$* is a $C_4$ to $C_{14}$ hydrocarbyl, preferably the residue of a $C_4$ to $C_{14}$ OXO-alcohol, that may be the same or different as $R_2$.

In a preferred embodiment of the invention in any formula described herein, $R^1$ is tolyl and $R^2$ is a $C_9$ or $C_{10}$ hydrocarbyl.

In a preferred embodiment of the invention in any formula described herein, $R^2$ is not linear, preferably $R^2$ is not a linear $C_4$ or $C_5$ hydrocarbyl, preferably $R^2$ is not a linear group containing 4 or 5 carbon atoms. In a preferred embodiment of the invention in any formula described herein, $R^2$ is branched or cyclic, preferably branched.

In a preferred embodiment of the invention, the compounds produced herein may be a mixture of two, three, four or more compounds produced herein at any ratio. In an embodiment of the invention, the first compound is present at 0.1 to 99.8 wt % (preferably 1 to 98 wt %, preferably 5 to 94.9 wt %, preferably 10 to 89.9 wt %), the second compound is present at 0.1 to 99.8 wt % (preferably 1 to 98 wt %, preferably 5 to 94.9 wt %, preferably 10 to 89.9 wt %), and each additional compound is present at least 0.1 wt %, preferably at least 1 wt %, preferably at least 5 wt %, preferably at least 10 wt %, based upon the weight of the plasticizer compounds.

In a preferred embodiment of the invention, the compounds produced herein are represented by the formula:

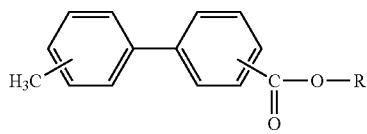

where R is a linear $C_6$ or $C_9$ hydrocarbyl, is derived from a $C_6$ or $C_9$ alcohol, or when R is the resulting structure from an OXO-alcohol, alternately R is linear and has 7, 8, 10, 11, 12 or 13 carbon atoms.

One route to non-phthalate plasticizers of the present disclosure is by combination of two benzene molecules, by controlled hydrogenation, as follows:

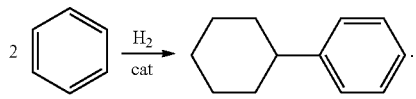

According to this method, the cyclohexyl benzene so formed can be optionally dehydrogenated to form biphenyl as follows:

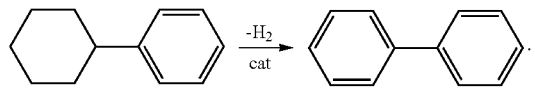

In either case, the aromatic ring(s) are subsequently alkylated with an alcohol, such as methanol, which acts to add one or more methyl groups to the ring(s), followed by oxygenation of the pendant methyl group(s) to form carboxylic acid group(s), and subsequently esterified with an alcohol, ROH, to form the mono- or diesters of the present disclosure and subsequently hydrogenated with an hydrogen over hydrogenation catalyst, to form one or more saturated ring:

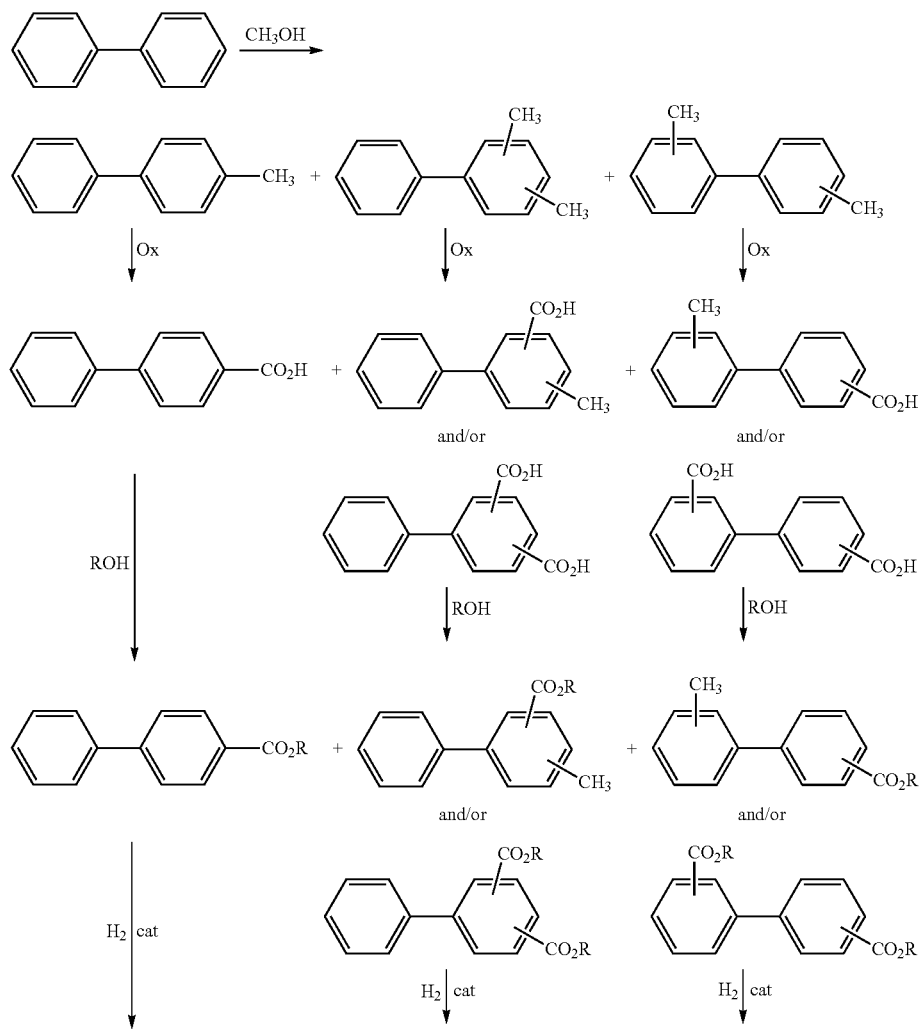

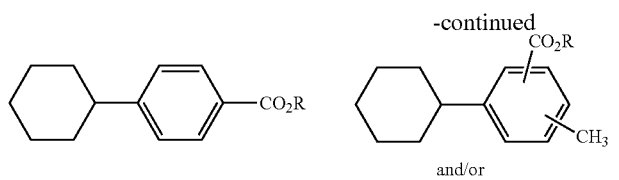
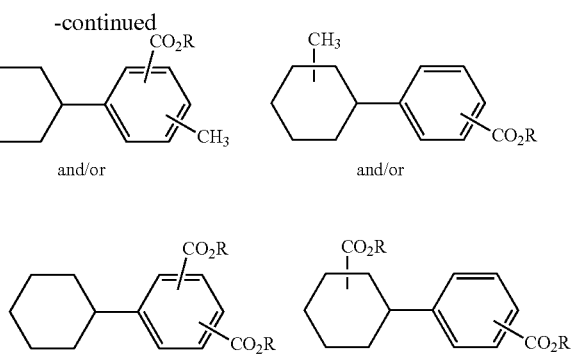

wherein ROH is a branched alcohol, preferably an OXO-alcohol, even more preferably a $C_4$ to $C_{14}$ OXO-alcohol.

Another route to non-phthalate plasticizers of the present disclosure is by oxidative coupling of two benzene molecules to form biphenyl, as follows: For benzene coupling: Ukhopadhyay, Sudip; Rothenberg, Gadi; Gitis, Diana; Sasson, Yoel. Casali Institute of Applied Chemistry, Hebrew University of Jerusalem, Israel. Journal of Organic Chemistry (2000), 65(10), pp. 3107-3110. Publisher: American Chemical Society, incorporated herein by reference.

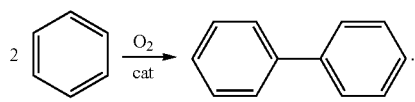

Similarly to the first process, the biphenyl molecule is then alkylated, for example, with an alcohol, such as methanol, to add one or more methyl groups to the ring(s), followed by oxygenation of the pendant methyl group(s) to form carboxylic acid group(s), and subsequently esterified with an alcohol, ROH, to form the mono- or diesters of the present disclosure and subsequently hydrogenated with an hydrogen over hydrogenation catalyst, to form one or more saturated ring.

Of course, a similar process can be followed utilizing an alkyl aromatic, such as toluene as the starting material in place of benzene:

wherein ROH is a branched alcohol, preferably an OXO-alcohol, even more preferably a $C_4$ to $C_{14}$ OXO-alcohol. Either monoesters or diesters can be formed, or both, depending on reaction conditions. Likewise, by appropriate control of the oxidation step so as to oxidize only one of the pendant methyl groups, monoester compounds of the following general formula can be formed:

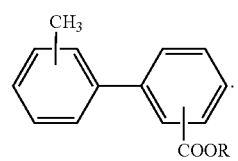

Alternatively, one mole of toluene can be hydrogenated to form methyl cyclohexene, and then the methyl cyclohexene used to alkylate another mole of toluene, followed by dehydrogenation to form dimethyl biphenyl.

In a more preferred embodiment, the resulting alkylated aromatic compound is oxidized to acid/diacid then esterified with OXO-alcohols, which are mixed linear and branched alcohol isomers, the formation of which is described in more detail below.

"OXO-alcohols" are isomeric mixtures of branched, organic alcohols. "OXO-esters" are compounds having at least one functional ester moiety within its structure derived from esterification of a carboxylic acid portion or moiety of a compound with an OXO-alcohol.

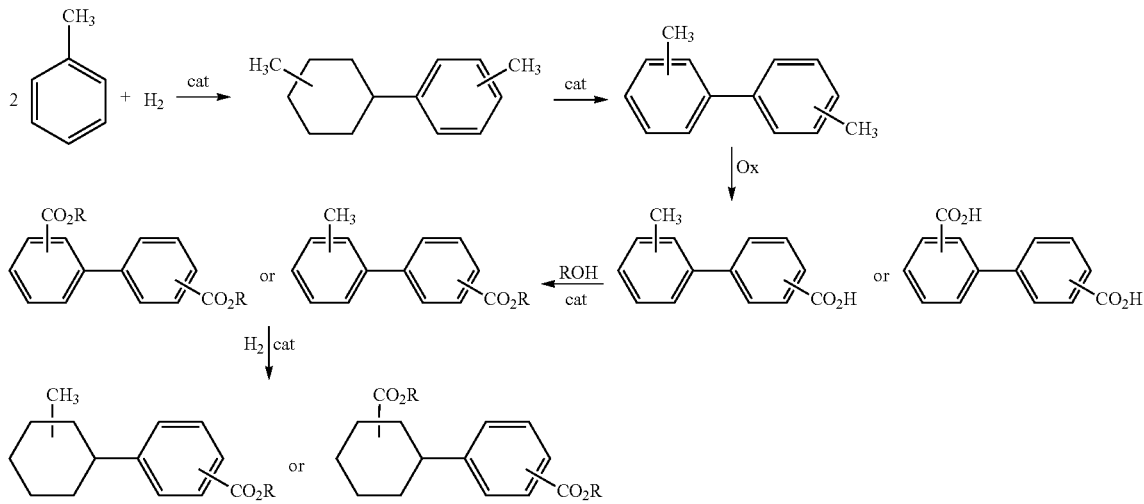

OXO-alcohols can be prepared by hydroformylating olefins, followed by hydrogenation to form the alcohols. "Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogeneous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, incorporated herein by reference in its entirety. Olefins for hydroformylation can also be prepared by dimerization of propylene or butenes through commercial processes such as the IFP Dimersol™ process or the Huls (Evonik) Octol™ process.

Branched aldehydes are then produced by hydroformylation of the isomeric olefins. The resulting branched aldehydes can then be recovered from the crude hydroformylation product stream by fractionation to remove unreacted olefins. These branched aldehydes can then be hydrogenated to form alcohols (OXO-alcohols). Single carbon number alcohols can be used in the esterification of the acids described above, or differing carbon numbers can be used to optimize product cost and performance requirements. The "OXO" technology provides cost advantaged alcohols. Other options are considered, such as hydroformylation of $C_4$-olefins to $C_5$-aldehydes, followed by hydrogenation to $C_5$-alcohols, or aldehyde dimerization followed by hydrogenation to $C_{10}$ alcohols.

"Hydrogenating" or "hydrogenation" is addition of hydrogen ($H_2$) to a double-bonded functional site of a molecule, such as in the present case the addition of hydrogen to the aldehyde moieties of a di-aldehyde, to form the corresponding di-alcohol, and saturation of the double bonds in an aromatic ring. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as, but not limited to Pt/C, Pt/$Al_2O_3$ or Pd/$Al_2O_3$ and Ni. Useful hydrogenation catalysts include platinum, palladium, ruthenium, nickel, zinc, tin, cobalt, or a combination of these metals, with palladium being particularly advantageous.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

In a preferred embodiment, this invention relates to a process for making compounds of the formula:

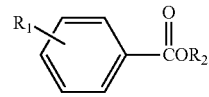

wherein $R_1$ is a cyclic hydrocarbon optionally substituted with an alkyl and/or an OXO-ester, and $R_2$ is a hydrocarbon residue of a $C_4$ to $C_{14}$ OXO-alcohol, comprising the steps of: reacting benzene or alkylated benzene under conditions appropriate to form alkylated biphenyl; optionally alkylating biphenyl to form said alkylated biphenyl; oxidizing the alkyl group(s) on said alkylated biphenyl to form at least one acid group; and reacting said acid group(s) with an OXO-alcohol under esterification conditions to form said compounds.

In a preferred embodiment of the invention, the reacting step is conducted with benzene, and said optional alkylating step is conducted with an alcohol (such as methanol).

In a preferred embodiment of the invention, the alkylating step is conducted in the presence of an acid catalyst.

In a preferred embodiment of the invention, the reacting step is conducted with benzene, further comprising the steps of: hydroalkylating benzene by reacting benzene in the presence of $H_2$ to hydrogenate one mole of said benzene to form cyclohexene, alkylating benzene with said cyclohexene to form cyclohexylbenzene; dehydrogenating said cyclohexylbenzene to form biphenyl; and alkylating one or both aromatic moieties of said biphenyl to form said alkylated biphenyl, where preferably the hydroalkylating step is conducted in the presence of a hydrogenation catalyst, the alkylating step is conducted with an alkylation catalyst, and the dehydrogenating step is conducted with a dehydrogenation catalyst.

In a preferred embodiment of the invention, the hydrogenation catalyst is selected from the group consisting of platinum, palladium, ruthenium, nickel, zinc, tin, cobalt, or a combination of these metals, with palladium being particularly advantageous; the alkylation catalyst is selected from the group consisting of Zeolite, mixed metal oxides and the dehydrogenation catalyst is selected from the group consisting of platinum, pladium, Ru, Rh, nickel, zinc, tin, cobalt and combinations thereof.

In a preferred embodiment of the invention, the reacting step is conducted with benzene in the presence of oxygen and an oxidative coupling catalyst, forming biphenyl, further comprising the step of: alkylating one or both aromatic moieties of said biphenyl to form said alkylated biphenyl, preferably the alkylating step is conducted with an alkylation catalyst.

In a preferred embodiment of the invention, the reacting step is conducted with toluene, further comprising the steps of: reacting toluene in the presence of $H_2$ and a hydrogenation catalyst to form methyl cyclohexene; reacting said methyl cyclohexene with toluene in the presence of an alkylation catalyst to form dimethyl cyclohexylbenzene; and dehydrogenating said dimethyl cyclohexylbenzene in the presence of a dehydrogenation catalyst to form the alkylated biphenyl, which is preferably dimethyl-biphenyl.

In a preferred embodiment of the invention, after reacting the acid group(s) with an OXO-alcohol under esterification conditions, the reaction product is contacted with a basic solution such as saturated sodium bicarbonate or a caustic soda wash.

In a preferred embodiment of the invention, the crude ester is further stripped to remove excess alcohol and the stripped plasticizer is treated with activated carbon to improve the liquid volume resistivity of the plasticizer.

As discussed above, the resulting OXO-alcohols can be used individually or together in alcohol mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol or acid used for the polar moiety end of the plasticizer, and to meet other plasticizer performance properties. The preferred OXO-alcohols are those having from 5 to 13 carbons, more preferably $C_5$ to $C_{11}$ alcohols, and even more preferably $C_6$ to $C_{10}$ alcohols.

In one embodiment the preferred OXO-alcohols are those which have an average branching of from 0.2 to 5.0 branches per molecule, and from 0.35 to 5.0 methyl branches per molecule, or even from 1.3 to 5.0 methyl branches per molecule. In a more preferred embodiment, the alcohols have from 0.05 to 0.4 branches per residue at the alcoholic beta carbon.

Typical branching characteristics of OXO-alcohols are provided in Table 1, below.

TABLE 1

$^{13}C$ NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.2 | 0 | 0.13 | 2.2 | — | 0.04 |
| $C_8$ | 8.0 | 0 | 0.08 | 2.6 | — | — |
| $C_9$ | 9.3 | 0 | 0.09 | 3.1 | — | — |
| $C_{10}$ | 10.1 | 0 | 0.08 | 3.1 | — | — |
| $C_{12}$ | 11.8 | 0 | 0.09 | 3.9 | — | — |
| $C_{13}$ | 12.7 | 0 | 0.09 | 3.9 | — | — |

— Data not available.
[a]—COH carbon.
[b]Branches at the —CCH$_2$OH carbon.
[c]This value counts all methyl groups, including $C_1$ branches, chain end methyls, and methyl endgroups on $C_2$+ branches.
[d]$C_1$ branches only.
[e]Calculated values based on an assumed molar isomeric distribution of 65% n-butanol and 35% isobutanol (2-methylpentanol).
[f]Calculated values based on an assumed molar isomeric distribution of 65% n-pentanol, 30% 2-methylbutanol, and 5% 3-methylbutanol.

In a preferred embodiment of the invention, the alcohol (such as an OXO-alcohol) has 2.0 to 3.5 methyl branches per molecule, typically 2.1 to 3.3.

In general, for every polymer to be plasticized, a plasticizer is required with a good balance of polarity or solubility, volatility and viscosity to have acceptable plasticizer compatibility with the resin. In particular, if the 20° C. kinematic viscosity is higher than 250 mm$^2$/sec as measured by the appropriate ASTM test, or alternately if the 20° C. cone-and-plate viscosity is higher than 250 cP, this will affect the plasticizer processability during formulation, and can require heating the plasticizer to ensure good transfer during storage and mixing of the polymer and the plasticizer. Volatility is also an important factor which affects the ageing or durability of the plasticized polymer. Highly volatile plasticizers will diffuse and evaporate from the plastic resin matrix, thus losing mechanical strength in applications requiring long term stability/flexibility. Relative plasticizer loss from a resin matrix due to plasticizer volatility can be roughly predicted by neat plasticizer weight loss at 220° C. using Thermogravimetric Analysis.

We have found that when $C_4$ to $C_{13}$ OXO-alcohols are used as reactants for the esterification reactions described above, the resulting OXO-esters are in the form of relatively high-boiling liquids (having low volatility), which are readily incorporated into polymer formulations as plasticizers.

Any of the esters can have $R_1$ and $R_2$ which contain mixed alkyl isomer residues of $C_4$ to $C_{13}$ OXO-alcohols, can be used as plasticizers for polymers, such as vinyl chloride resins, polyesters, polyurethanes, silylated polymers, polysulfides, acrylics, ethylene-vinyl acetate copolymer, rubbers, poly(meth)acrylics and combinations thereof, preferably polyvinylchloride.

In a preferred embodiment, this invention relates to polymer composition comprising a thermoplastic polymer and at least one plasticizer described herein, such as a plasticizer of the formula:

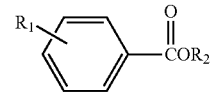

wherein $R_1$ is a saturated or unsaturated cyclic hydrocarbon optionally substituted with an alkyl and/or an OXO-ester, and $R_2$ is a hydrocarbon residue of a $C_4$ to $C_{14}$ OXO-alcohol, preferably where the thermoplastic polymer is selected from the group consisting of vinyl chloride resins, polyesters, polyurethanes, ethylene-vinyl acetate copolymer, rubbers, poly(meth)acrylics and combinations thereof, alternately the polymer is selected from the group consisting of polyvinyl chloride (PVC), polyvinylidene chloride, a copolymer of polyvinyl chloride and polyvinylidene chloride, and polyalkyl methacrylate (PAMA), preferably the polymer is a copolymer of vinyl chloride with at least one monomer selected from the group consisting of vinylidene chloride, vinyl acetate, vinyl propionate, vinyl butyrate, vinyl benzoate, methyl acrylate, ethyl acrylate, and butyl acrylate.

In any embodiment of the invention, in the polymer composition comprising a thermoplastic polymer and at least one plasticizer, the amount of plasticizer is from 5 to 90 wt %, based upon the weight of the polymer and plasticizer, preferably from 10 to 100 wt %, even more preferably in the range from 15 to 90 wt %, preferably in the range from 20 to 80 wt %.

The polymer composition comprising a thermoplastic polymer and at least one plasticizer described herein may optionally contain further additional plasticizers other than those produced herein, such as: dialkyl (ortho)phthalate, preferably having 4 to 13 carbon atoms in the alkyl chain; trialkyl trimellitates, preferably having 4 to 10 carbon atoms in the side chain; dialkyl adipates, having 4 to 13 carbon atoms; dialkyl sebacates preferably having 4 to 13 carbon atoms; dialkyl azelates preferably having 4 to 13 carbon atoms; preferably dialkyl terephthalates each preferably having 4 to 8 carbon atoms and more particularly 4 to 7 carbon atoms in the side chain; alkyl 1,2-cyclohexanedicarboxylates, alkyl 1,3-cyclohexanedicarboxylates and alkyl 1,4-cyclohexanedicarboxylates, and preferably here alkyl 1,2-cyclohexanedicarboxylates each preferably having 4 to 13 carbon atoms in the side chain; dibenzoic esters of glycols; alkylsulfonic esters of phenol with preferably one alkyl radical containing 8 to 22 carbon atoms; polymeric plasticizers (based on polyester in particular), glyceryl esters, acetylated glycerol esters, epoxy estolide fatty acid alkyl esters, citric triesters having a free or carboxylated OH group and for example alkyl radicals of 4 to 9 carbon atoms, alkylpyrrolidone derivatives having alkyl radicals of 4 to 18 carbon atoms and also alkyl benzoates, preferably having 7 to 13 carbon atoms in the alkyl chain. In all instances, the alkyl radicals can be linear or branched and the same or different.

The polymer composition comprising a thermoplastic polymer and at least one plasticizer described herein prepared according to the present invention may further contain additives to optimize the chemical, mechanical or processing properties, said additives being more particularly selected from the group consisting of fillers, such as calcium carbonate, titanium dioxide or silica, pigments, thermal stabilizers, antioxidants, UV stabilizers, lubricating or slip agents, flame retardants, antistatic agents, biocides, impact modifiers, blowing agents, (polymeric) processing aids, viscosity depressants or regulators such as thickener and thinners, antifogging agents, optical brighteners, etc.

Thermal stabilizers useful herein include all customary polymer stabilizers, especially PVC stabilizers in solid or liquid form, examples are those based on Ca/Zn, Ba/Zn, Pb, Sn or on organic compounds (OBS), and also acid-binding phyllosilicates such as hydrotalcite. The mixtures to be used according to the present invention may have a thermal stabilizer content of 0.5 to 10, preferably 0.8 to 5 and more preferably 1.0 to 4 wt %, based upon the weight of the polymer composition.

It is likewise possible to use costabilizers with plasticizing effect in the polymer composition comprising a thermoplastic polymer and at least one plasticizer as described herein, in particular epoxidized vegetable oils, such as epoxidized linseed oil or epoxidized soya oil.

Antioxidants are also useful in the polymer composition comprising a thermoplastic polymer and at least one plasticizer described herein and can include sterically hindered amines—known as HALS stabilizers, sterically hindered phenols, such as Topanol™ CA, phosphites, UV absorbers, e.g. hydroxybenzophenones, hydroxyphenylbenzotriazoles and/or aromatic amines. Suitable antioxidants for use in the compositions of the present invention are also described for example in "Handbook of Vinyl Formulating" (editor: R. F. Grossman; J. Wiley & Sons; New Jersey (US) 2008). The level of antioxidants in the mixtures of the present invention is typically not more than 10 pph, preferably not more than 8 pph, more preferably not more than 6 pph and even more preferably between 0.01 and 5 pph (pph=parts per hundred parts of polymer).

Organic and inorganic pigments can be also used in the polymer composition comprising a thermoplastic polymer and at least one plasticizer as described herein. The level of pigments in the compositions to be used according to the present invention is typically not more than 10 pph, preferably in the range from 0.01 to 5 pph and more preferably in the range from 0.1 to 3 pph. Examples of useful inorganic pigments are $TiO_2$, CdS, $CoO/Al_2O_3$, $Cr_2O_3$. Examples of useful organic pigments are for example azo dyes, phthalocyanine pigments, dioxazine pigments and also aniline pigments.

The polymer composition comprising a thermoplastic polymer and at least one plasticizer described herein may contain one or more filler, including mineral and/or synthetic and/or natural, organic and/or inorganic materials, for example, calcium oxide, magnesium oxide, calcium carbonate, barium sulphate, silicon dioxide, phyllosilicate, carbon black, bitumen, wood (e.g. pulverized, as pellets, micropellets, fibers, etc.), paper, natural and/or synthetic fibers, glass, etc.

The compositions described herein can be produced in various ways. In general, however, the composition is produced by intensively mixing all components in a suitable mixing container at elevated temperatures. The plastic pellet or powder (typically suspension PVC, microsuspension PVC or emulsion PVC) is typically mixed mechanically, i.e. for example in fluid mixers, turbomixers, trough mixers or belt screw mixers with the plasticizer and the other components at temperatures in the range from 60° C. to 140° C., preferably in the range from 80° C. to 100° C. The components may be added simultaneously or, preferably, in succession (see also E. J. Wickson "Handbook of PVC Formulating", John Wiley and Sons, 1993, pp. 747 ff). The blend of PVC, plasticizer and other additive as described above (e.g. the PVC compound or the PVC paste) is subsequently sent to the appropriate thermoplastic moulding processes for producing the finished or semi-finished article, optionally a pelletizing step is interposed.

The blends (e.g. the PVC compound or the PVC paste) are particularly useful for production of garden hoses, pipes, and medical tubing, floor coverings, flooring tiles, films, sheeting, roofing, or roofing webs, pool liners, building protection foils, upholstery, and cable sheathing and wire insulation, particularly wire and cable coating, coated textiles and wall coverings.

The plasticizers of the invention are useful across the range of plasticized polyvinyl chloride materials. The plasticizers of the invention are useful in the production of semi-rigid polyvinyl chloride compositions which typically contain from 10 to 40 pph, preferably 15 to 35 pph, more preferably 20 to 30 pph of plasticizer (pph=parts per hundred parts PVC); flexible polyvinyl chloride compositions which typically contain from 40 to 60 pph, preferably 44 to 56 pph, more preferably from 48 to 52 pph plasticizer; and highly flexible compositions which typically contain from 70 to 110 pph, preferably 80 to 100 pph, more preferably 90 to 100 pph of plasticizer.

One widespread use of polyvinyl chloride is as a plastisol. A plastisol is a fluid or a paste consisting of a mixture of polyvinyl chloride and a plasticizer optionally containing various additives, such as those described above. A plastisol is used to produce layers of polyvinyl chloride which are then fused to produce coherent articles of flexible polyvinyl chloride. Plastisols are useful in the production of flooring, tents, tarpaulins, coated fabrics such as automobile upholstery, in car underbody coatings, in mouldings and other consumer products. Plastisols are also used in footwear, fabric coating, toys, flooring products and wallpaper. Plastisols typically contain 40 to 200 pph, more typically 50 to 150 pph, more typically 70 to 120 pph, more typically 90 to 110 pph of plasticizer.

In a preferred embodiment of the invention, one or more (such as two or three) plasticizers produced herein are combined with a polymer such as PVC to form a PVC compound (typically made from suspension PVC) or a PVC paste (typically made from an emulsion PVC). A particularly useful PVC in the PVC compound or paste is one having a K value above 70. Particularly preferred PVC compounds or paste comprise: 20 to 100 pph plasticizer(s) and/or 0.5 to 15 pph stabilizer(s), and/or 1 to 30 pph, preferably 15 to 30 pph, filler(s), even more preferably the filler is calcium carbonate and the stabilizer is a calcium/zinc stabilizer. The above combination is useful in wire and cable coatings, particularly automobile wire and cable coating and or building wire insulation.

In general, a particularly good (i.e. low) glass transition temperature is achievable for the polymer compositions of the present invention by using plasticizer which itself has a low glass transition temperature and/or by using a high plasticizer content. Polymer compositions of the present invention may have glass transition temperatures in the range from −70° C. to +10° C., preferably in the range from −60° C. to −5° C., more preferably in the range from −50° C. to −20° C. and most preferably in the range from −45° C. to −30° C. Tg of the polymer composition is determined using DMTA and DSC, as described below (In the event of conflict between the DMTA and DSC results, DMTA shall be used). Tg of the neat plasticizer is determined using DSC as described below.

EXPERIMENTAL

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure can be practiced otherwise than as specifically described herein.

EXAMPLES

General Procedure for Esterification

Into a four necked 1000 ml round bottom flask equipped with an air stirrer, nitrogen inductor, thermometer, Dean-Stark trap and chilled water cooled condenser were added an aromatic mono or (di)acid, and the OXO-alcohol(s). The Dean-Stark trap was filled with the OXO-alcohol(s). The reaction mixture was heated to 220° C. with air stirring under a nitrogen sweep. The water that was produced was collected in the Dean-Stark trap and was drained frequently. The theoretical weight of water was obtained in 3 hours at 220° C. indicating 96% conversion. The reaction mixture was heated longer to achieve complete conversion to the diester. Excess alcohols plus some monoesters (in the case of diester synthesis) were removed by distillation. The crude residual product was optionally treated with decolorizing charcoal with stirring at room temperature overnight. The mixture was then filtered twice to remove the charcoal.

Example 1: Esterification of 4-phenyl-benzoic acid with OXO-$C_{10}$ alcohols

Into a 4-necked 500 ml round bottom flask equipped with an air stirrer, thermometer, $N_2$ inductor, Dean-Stark trap and chilled water cooled condenser were added 4-phenyl-benzoic acid (101.8 g, 0.514 mole), OXO-$C_{10}$ alcohols (163 g, 1.027 mole), and OXO-$C_{10}$ alcohols (15.5 g, 0.098 moles) were added to the Dean-Stark trap. The reaction mixture was heated for a total of 13 hours at 208-220° C. with gas chromatographic (GC) sampling. The product was then concentrated using a Claisen adapter, chilled water cooled condenser and receiving flask. The crude product was a clear light yellow liquid, 99.5% purity by GC.

Example 2: Esterification of 4-phenylbenzoic acid with OXO-$C_9$ alcohols

Into a 4-necked 500 ml round bottom flask equipped with an air stirrer, thermometer, N2 inductor, Dean-Stark trap and chilled water cooled condenser were added 4-phenylbenzoic acid (138 g, 0.6962 mole), OXO-$C_9$ alcohols (201.1 g, 1.3924 mole) and xylenes (21.5 g, 0.202 mole). The reaction mixture was heated for a total of 7 hours at 185-220° C. with GC sampling. The product was concentrated using a Claisen adapter, chilled water cooled condenser and receiving flask. The concentrated product was dissolved in an equal weight of toluene (180 g) and was washed twice with 100 g of a 3 wt % sodium hydroxide solution followed by distilled water (100 g). The upper toluene phase was then dried over magnesium sulfate, filtered and the toluene removed on a rotary evaporator. The concentrated product was a clear and colorless liquid with a purity of 99.5% monoesters by GC.

Example 3: Esterification of 3-phenyl-benzoic acid with OXO-$C_{10}$ alcohols

Into a 4-necked 500 ml round bottom flask equipped with an air stirrer, thermometer, $N_2$ inductor, Dean-Stark trap and chilled water cooled condenser were added biphenyl-3-carboxylic acid (50.0 g, 0.2522 mole), OXO-$C_{10}$ alcohols (79.7 g, 0.5044 mole), and xylenes (75 g, 0.706 moles) were added to the Dean-Stark trap. The reaction mixture was heated for a total of 19 hours at 156-192° C. The product was concentrated using a Claisen adapter, chilled water cooled condenser and receiving flask. The concentrated product was dissolved in an equal weight of toluene (77 g) and was washed three times with 25 g of a 3 wt % sodium hydroxide solution followed by distilled water (25 g) twice. The upper toluene phase was then dried over magnesium sulfate, filtered and distilled overhead. The boiling point of the pure product was 175-183° C./0.27-0.28 mm vacuum. The purity of the distilled product was 99.2% by GC.

Example 4: Esterification of 2-phenyl-benzoic acid with OXO-$C_9$ alcohols

Into a 4-necked 500 ml round bottom flask equipped with an air stirrer, thermometer, $N_2$ inductor, Dean-Stark trap and chilled water cooled condenser were added biphenyl-2-carboxylic acid (99.4 g, 0.502 mole), OXO-$C_9$ alcohols (144.4 g, 1.003 mole), and OXO-$C_9$ alcohols (20 g, 0.14 moles) were added to the Dean-Stark trap. The reaction mixture was heated for a total of 7 hours at 205-208° C. with GC sampling. The product was distilled using a Claisen adapter, chilled water cooled condenser and receiving flask. Two of the heart cuts were combined and dissolved in an equal weight of toluene (121.7 g) and were washed twice with 50 g of a 3 wt % sodium hydroxide solution followed by distilled water (50 g). The upper toluene phase was then dried over magnesium sulfate, filtered then treated with decolorizing charcoal with stirring at room temperature for 2 hours. The product was filtered twice to remove all the charcoal. The toluene was then removed on the rotary evaporator. The clear and colorless product was isolated and had a purity of 99.5% (by GC) monoesters.

Example 5: Blend of Example 1, 3 and 4

The following blend of pure monoesters was prepared: the ortho ester or biphenyl-2-carboxylic acid plus OXO-$C_9$ alcohols (7.5 grams or 25 wt %), the meta ester biphenyl-3-carboxylic acid plus OXO-$C_{10}$ alcohols (15.0 grams or 50 wt %) and the para monoester or biphenyl-4-carboxylic acid plus OXO-$C_{10}$ alcohols (7.5 grams or 25 wt %).

Example 6: Esterification of 4-cyclohexyl benzoic acid with OXO-$C_{10}$ alcohols Into a 4-necked 500 ml round bottom flask equipped with an air stirrer, thermometer, $N_2$ inductor, Dean-Stark trap and chilled water cooled condenser were added 4-cyclohexyl benzoic acid (100.64 g, 0.493 mole), OXO-$C_{10}$ alcohols (156.5 g, 0.986 mole), and OXO-$C_{10}$ alcohols (15.5 g, 0.098 moles) were added to the Dean-Stark trap. The reaction mixture was heated for a total of 10 hours at 217-220° C. with GC sampling. The product was then concentrated using a Claisen adapter, chilled water cooled condenser and receiving flask. The crude product was a clear & colorless liquid, 99.2% purity (by GC).

Example 7: Blend of Example 1 and 6

The following four blends (by weight) were prepared containing the monoester of 4-phenylbenzoic acid plus OXO-$C_{10}$ alcohols (example 1) and the monoester of 4-cyclohexylbenzoic acid plus OXO-$C_{10}$ alcohols (example 6):
7a: blend of example 1 (70%) plus example 6 (30%),
7b: blend of example 1 (70%) plus example 6 (30%),
7c: blend of example 1 (50%) plus example 6 (50%),
7d: blend of example 1 (30%) plus example 6 (70%).

Example 8: Esterification of 4'-methylbiphenyl-4-carboxylic acid with OXO-$C_9$ alcohols Into a 4-necked 500 ml round bottom flask equipped with an air stirrer, thermometer, $N_2$ inductor, Dean-Stark trap and chilled water cooled condenser were added 4-methylbiphenyl-4-carboxylic acid (100 g, 0.47114 mole), OXO-$C_9$ alcohols (136.1 g, 0.9423 mole) and toluene (50 g, 0.54 mole). The reaction mixture was heated for a total of 6 hours at 187-221° C. with GC sampling. The product was then distilled using a Claisen adapter, chilled water cooled condenser and receiving flask. The product distilled at 184-185° C./0.10 mm and was a clear, essentially colorless liquid with 99.6% purity (by GC).

Example 9: Esterification of 4'-methylbiphenyl-2-carboxylic acid with OXO-$C_9$ alcohols Into a 4-necked 1000 ml round bottom flask equipped with an air stirrer, thermometer, $N_2$ inductor, Dean-Stark trap and chilled water cooled condenser were added 2-(p-tolyl)benzoic acid (191.9 g, 0.9042 mole), OXO-$C_9$ alcohols (261.12 g, 1.8087 mole) and xylenes (19.4 g, 0.18 mole). The reaction mixture was heated for a total of 22 hours at 207-214° C. with GC sampling. The product was then distilled using a Claisen adapter, chilled water cooled condenser and receiving flask. The product distilled at 145-162° C./0.10 mm and was a clear, essentially colorless liquid of 99.86% purity (by GC).

Example 10: Esterification of 2'-methyl-3-biphenylcarboxylic acid with OXO-$C_{10}$ alcohols Into a 4-necked 500 ml round bottom flask equipped with an air stirrer, thermometer, $N_2$ inductor, Dean-Stark trap and chilled water cooled condenser were added 2'-methyl-3-biphenylcarboxylic acid (51 g, 0.24 mole), OXO-$C_{10}$ alcohols (76 g, 0.481 mole) and xylenes (34.3 g, 0.323 mole). The reaction mixture was heated for a total of 15 hours at 145-182° C. with GC sampling. The product was concentrated using a Claisen adapter, chilled water cooled condenser and receiving flask. The concentrated product was dissolved in an equal weight of toluene (63.1 g) and was washed twice with 30 g of a 3 wt % sodium hydroxide solution followed by distilled water (30 g). The upper toluene phase was then dried over magnesium sulfate, filtered and distilled. The monoester distilled at Bp=175-182° C./0.10 mm. A clear off white liquid was obtained with a purity of 99.42% (by GC).

Example 11: Preparation of 4'-methyl-3-biphenylcarboxylic acid with OXO-$C_{10}$ alcohols Decyl 3-bromobenzoate was prepared from the condensation of 3-bromobenzoic acid and OXO-$C_{10}$ alcohols by refluxing in benzene with $H_2SO_4$ and water removal via a Dean-Stark trap with subsequent wash with basic solution (sodium bicarbonate). The ester was purified by distillation: $^1$H NMR (400 MHz, $CDCl_3$) δ 0.87-1.77 (m, 21H), 4.32 (m, 2H), 7.32 (m, 1H), 7.67 (m, 1H), 7.98 (m, 1H), 8.18 (s, 1H). In a 3-neck flask, decyl 3-bromobenzoate (1 equiv) and p-tolylboronic acid (1.2 equiv) were dissolved in toluene to make a 0.2 M solution with respect to the bromobenzoic ester and the mixture degassed with $N_2$. A 2 M, degassed solution of sodium carbonate (2.5 equiv) in $H_2O$:MeOH (4:1) was added. Palladium tetrakistriphenylphosphine (0.01 equiv) was added and the mixture refluxed until completion. The reaction was cooled and the layers separated. The aqueous layer was extracted with ethyl acetate and combined organic layers were washed with brine, dried over $MgSO_4$, filtered and concentrated under reduced pressure. Purification of the resulting crude oil was achieved by vacuum distillation $^1$H NMR (400 MHz, $CDCl_3$) δ 0.80-1.87 (m, 20H), 2.45 (s, 3H), 4.39 (m, 2H), 7.31 (d, J=8.0 Hz, 2H), 7.56 (m, 3H), 7.80 (m, 1H), 8.05 (m, 1H), 8.32 (s, 1H).

Example 12: Preparation of 2'-methyl-4-biphenylcarboxylic acid with OXO-$C_{10}$ alcohols Decyl 4-bromobenzoate was prepared from the condensation of 4-bromobenzoic acid and OXO-$C_{10}$ alcohols by refluxing in benzene with $H_2SO_4$ and water removal via a Dean-Stark trap with subsequent wash with basic solution (sodium bicarbonate) then purified by distillation. Decyl 2-bromobenzoate was coupled with o-tolylboronic acid as described in Example 11. Spectral data is as follows: decyl 2'-methylbiphenyl-4-carboxylate: $^1$H NMR (400 MHz, $CDCl_3$) 0.85-1.91 (m, 19H), 2.33 (s, 3H), 4.43 (m, 2H), 7.30 (m, 4H), 7.44 (d, J=8.0 Hz, 2H), 8.15 (m, 2H).

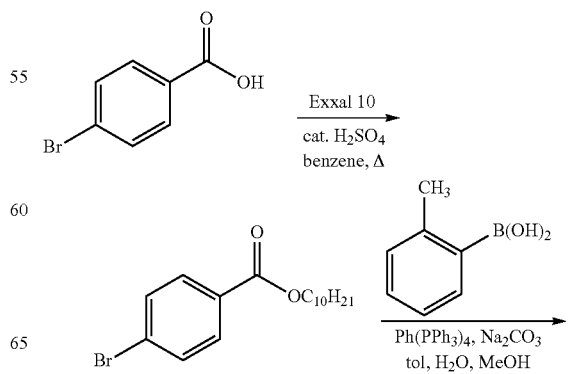

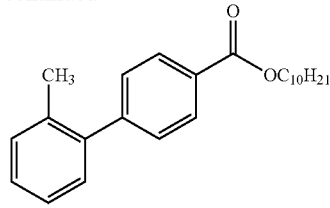

Example 13: Preparation of 3'-methyl-4-biphenylcarboxylic acid with OXO-$C_{10}$ alcohols Decyl 4-bromobenzoate was prepared from the condensation of 4-bromobenzoic acid and OXO-$C_{10}$ alcohols by refluxing in benzene with $H_2SO_4$ and water removal via a Dean-Stark trap with subsequent wash with basic solution (sodium bicarbonate): $^1$H NMR (400 MHz, $CDCl_3$) δ 0.86-1.76 (m, 20H), 4.30 (m, 2H), 7.57 (d, J=8.0 Hz, 2H), 7.90 (dd, J=2.2, 8.6 Hz, 2H). Decyl 4-bromobenzoate was coupled with m-tolylboronic acid as described in Example 11: $^1$H NMR (400 MHz, $CDCl_3$) δ 0.88-1.80 (m, 19H), 2.44 (s, 3H), 4.33 (m, 2H), 7.22 (d, J=8.0 Hz, 1H), 7.36 (m, 1H), 7.45 (m, 1H), 7.66 (d, J=8.0 Hz, 2H), 8.11 (m, 2H); $^{13}$C NMR (100 MHz, $CDCl_3$) 10.9-39.4 (9C), 21.7, 65.3, 124.5-130.2 (8C), 138.7 (2C), 140.2, 145.8, 166.8.

Example 14: Preparation of 3'-methyl-4-biphenylcarboxylic acid with OXO-$C_9$ alcohols Nonyl 4-bromobenzoate was prepared from the condensation of 4-bromobenzoic acid and OXO-$C_9$ alcohols by refluxing in benzene with $H_2SO_4$ and water removal via a Dean-Stark trap with subsequent wash with basic solution (sodium bicarbonate): $^1$H NMR (400 MHz, $CDCl_3$) δ 0.87-1.78 (m, 19H), 4.31 (m, 2H), 7.57 (d, J=8.4 Hz, 2H), 7.90 (dd, J=2.9, 9.4 Hz, 2H). Nonyl 4-bromobenzoate was coupled with m-tolylboronic acid as described in Example 11: $^1$H NMR (400 MHz, $CDCl_3$) δ 0.90-1.78 (m, 19H), 2.45 (s, 3H), 4.38 (m, 2H), 7.22 (d, J=8.4 Hz, 1H), 7.36 (m, 1H), 7.45 (m, 2H), 7.66 (d, J=8.0 Hz, 2H), 8.11 (m, 2H); $^{13}$C NMR (100 MHz, $CDCl_3$) 10.9-39.4 (8C), 21.7, 65.6, 124.5-130.2 (8C), 138.7 (2C), 140.2, 145.8, 166.8.

Example 15: Preparation of 3'-methyl-2-biphenylcarboxylic acid with OXO-$C_{10}$ alcohols Decyl 2-bromobenzoate was prepared from the condensation of 2-bromobenzoic acid and OXO-$C_{10}$ alcohols by refluxing in benzene with $H_2SO_4$ and water removal via a Dean-Stark trap with subsequent wash with basic solution (sodium bicarbonate): $^1$H NMR (400 MHz, $CDCl_3$) δ 0.86-1.78 (m, 23H), 4.33 (m, 2H), 7.35 (m, 2H), 7.65 (m, 1H), 7.78 (d, J=8.0 Hz, 1H). Decyl 2-bromobenzoate was coupled with m-tolylboronic acid as described in Example 11: $^1$H NMR (400 MHz, $CDCl_3$) δ 0.72-1.39 (m, 21H), 2.42 (s, 3H), 4.07 (m, 2H), 7.18 (m, 3H), 7.30 (m, 1H), 7.41 (m, 2H), 7.53 (m, 1H), 7.85 (d, J=8.0 Hz, 1H).

Example 16: Preparation of 3'-methyl-3-biphenylcarboxylic acid with OXO-$C_{10}$ alcohols Decyl 3-bromobenzoate was coupled with m-tolylboronic acid as described in Example 11: $^1$H NMR (400 MHz, $CDCl_3$) δ 0.89-1.81 (m, 21H), 2.45 (s, 3H), 4.37 (m, 2H), 7.22 (d, J=8.0 Hz, 1H), 7.37 (t, J=8.0 Hz, 1H), 7.45 (d, J=8.0 Hz, 2H), 7.52 (t, J=8.0 Hz, 1 H), 7.79 (d, J=8.0 Hz, 1H), 8.03 (d, J=8.0 Hz, 1H), 8.29 (s, 1H); $^{13}$C NMR (100 MHz, $CDCl_3$) 11.6-3.4 (20C), 21.7, 65.4, 124.4 (2C), 128.1, 128.4 (2C), 128.6 (2C), 128.9, 129.0, 131.2, 131.6 (2C), 166.9.

Example 17: Preparation of Mixed Blend Monoesters of Methylbiphenyl Carboxylic Acids+Oxo Alcohols The following three monoesters were combined: 4-methylbiphenyl-4-oxo$C_9$ ester (example 8) (17.62 g), 2-methylbiphenyl-3-oxo$C_{10}$ ester (example 10) (3.86 g), and 4-methylbiphenyl-2-oxo$C_9$ ester (example 9) (3.95 g).

Example 18: Esterification of 2,2'-biphenyl dicarboxylic acid with $C_5$ alcohols (65/35, 1-pentanol/2-methyl-1-butanol)

Into a 4-necked 500 ml round bottom flask equipped with an air stirrer, thermometer, $N_2$ inductor, Dean-Stark trap and chilled water cooled condenser were added 2,2'-biphenyl dicarboxylic acid (100 g, 0.46 mole), and mixed $C_5$ alcohols (65/35, 1-pentanol/2-methyl-1-butanol) (165.0 g, 1.875 mole) to approximate the component distribution of an OXO-$C_5$ alcohol. The reaction mixture was heated for a total of 73 hours at 137-169° C. with GC sampling. The product was concentrated using a Claisen adapter, chilled water cooled condenser and receiving flask. The concentrated product was dissolved in an equal weight of toluene (140 g) and was washed twice with 50 g of a 3 wt % sodium hydroxide solution followed by distilled water (50 g). The upper toluene phase was then dried over magnesium sulfate, filtered and distilled. The diester distilled at Bp=174-184° C./0.10 mm. The purity obtained by GC analysis was 99.1%. The distillate was clear yellow liquid and was treated with decolorizing charcoal with stirring at room temperature for 2 hours. The product was filtered twice to remove all the charcoal. Clear and colorless sample was obtained.

Example 19: Esterification of 2,2'-biphenyl dicarboxylic acid with $C_6$ alcohols (65/35, 1-hexanol/2-methyl-1-pentanol)

Into a 4-necked 500 ml round bottom flask equipped with an air stirrer, thermometer, $N_2$ inductor, Dean-Stark trap and chilled water cooled condenser were added 2,2'-biphenyl dicarboxylic acid (199.3 g, 0.823 mole), and $C_6$ alcohols (65/35, 1-hexanol/2-methyl-1-pentanol) (336.2 g, 3.2903 mole) to approximate the component distribution of an OXO-$C_6$ alcohol. The reaction mixture was heated a total of 24 hours at 150-155° C. with GC sampling. The product was concentrated using a Claisen adapter, chilled water cooled condenser and receiving flask. The concentrated product was dissolved in an equal weight of toluene (347 g) and was washed twice with 100 g of a 3 wt % sodium hydroxide solution followed by distilled water (100 g). The upper toluene phase was then dried over magnesium sulfate, filtered and distilled. The diester distilled at Bp=189-191° C./0.10 mm. The distillates were clear yellow liquids and were dissolved in toluene then treated with decolorizing charcoal with stirring at room temperature for 2 hours. The product was filtered twice to remove all the charcoal then distilled overhead. A clear off white liquid was obtained Bp=184° C./0.10 mm with a purity of 97.9% (by GC).

Example 20: Esterification of 2,2'-biphenyl dicarboxylic acid with OXO-C₉ alcohols Into a 4-necked 500 ml round bottom flask equipped with an air stirrer, thermometer, N₂ inductor, Dean-Stark trap and chilled water cooled condenser were added 2,2'-biphenyl dicarboxylic acid (54.4 g, 0.252 mole), and OXO-C₉ alcohols (145.4 g, 1.01 mole) and xylenes (50 g, 0.47 mole). The reaction mixture was heated a total of 24 hours at 172-189° C. with GC sampling. The product was concentrated using a Claisen adapter, chilled water cooled condenser and receiving flask. The concentrated product was dissolved in an equal weight of toluene (99.7 g) and was washed three times with 50 g of a 3 wt % sodium hydroxide solution followed by distilled water (50 g) twice. The upper toluene phase was then dried over magnesium sulfate, filtered and distilled. The diester distilled at Bp=237° C./0.25-0.30 mm. The distillates were clear yellow orange liquids and were distilled a second time at 206-215° C./0.22-0.16 mm vacuum. The distillate remained yellow so it was dissolved in toluene then treated with decolorizing charcoal with stirring at room temperature for 2 hours. The product was filtered twice to remove all the charcoal. A clear light yellow liquid was obtained with a purity of 99.4% by GC.

Example 21: Preparation of Dihexylbiphenyl 4,4'Dicarboxylate Using Linear-C₆ Alcohols Hexyl 4-bromobenzoate was prepared from the condensation of 4-bromobenzoic acid and hexanol by refluxing in benzene with H₂SO₄ and water removal via a Dean-Stark trap with subsequent wash with basic solution (sodium bicarbonate). The ester was purified by distillation.

Under N₂, hexyl 4-bromobenzoate (1 equiv), bispinacolatodiboron (0.5 equiv), potassium carbonate (3 equiv) and PdCl₂ dppf (0.02 equiv) were dissolved in DMSO to make a 0.15 M solution with respect to the bromobenzoic ester. The solution was degassed with N₂, then heated at 80° C. overnight. Water and ethyl acetate were then added to the cooled reaction and the layers separated. The organic layer was extracted with ethyl acetate, then the combined organic layers washed with 10% HCl, water and brine. It was then dried (MgSO₄), filtered and concentrated. The crude oil was purified by passage through a short silica gel column (eluting with 10:90 acetone:petroleum ether) and vacuum distillation.

Example 22: Preparation of dihexyl biphenyl-3,3'-dicarboxylate using OXO-C₆ alcohols Hexyl 3-bromobenzoate was prepared from the condensation of 3-bromobenzoic acid and OXO hexanol by refluxing in benzene with H₂SO₄ and water removal via a Dean-Stark trap with subsequent wash with basic solution (sodium bicarbonate). The ester was purified by distillation: ¹H NMR (400 MHz, CDCl₃) δ 0.90 (m, 3H), 1.34 (m, 6H), 1.76 (m, 2H), 4.31 (t, J=6.6 Hz, 2H), 7.30 (t, J=8.0 Hz, 1H), 7.65 (m, 1H), 7.95 (m, 1H), 8.16 (s, 1H); ¹³C NMR (100 MHz, CDCl₃) 14.1, 22.6, 25.8, 28.8, 31.6, 65.7, 122.6, 128.2, 130.0, 132.6, 132.7, 135.9, 165.4. Under N₂, hexyl 3-bromobenzoate (1 equiv), bispinacolatodiboron (0.5 equiv), potassium carbonate (3 equiv) and PdCl₂ dppf (0.02 equiv) were dissolved in DMSO to make a 0.15 M solution with respect to the bromobenzoic ester. The solution was degassed with N₂, then heated at 80° C. overnight. Water and ethyl acetate were then added to the cooled reaction and the layers separated. The organic layer was extracted with ethyl acetate, then the combined organic layers washed with 10% HCl, water and brine. It was then dried (MgSO₄), filtered and concentrated. The crude oil was purified by passage through a short silica gel column (eluting with 10:90 acetone:petroleum ether) and vacuum distillation: ¹H NMR (400 MHz, CDCl₃) δ 0.91 (m, 6H), 1.36 (m, 12H), 1.80 (m, 4H), 4.36 (t, J=6.6 Hz, 2H), 7.54 (m, 2H), 7.81 (m, 2H), 8.06 (d, J=8.0 Hz, 2H), 8.30 (s, 2H); ¹³C NMR (100 MHz, CDCl₃) 14.2 (2C), 22.7 (2C), 25.9 (2C), 28.9 (2C), 31.6 (2C), 65.5 (2C), 128.4-131 (8C), 140.6 (4C), 166.6 (2C).

Example 23: Preparation of dihexyl biphenyl-3,4'-dicarboxylate using OXO-C₆ alcohols Hexyl 4-bromobenzoate was prepared from the condensation of 4-bromobenzoic acid and OXO-C₆ alcohols by refluxing in benzene with H₂SO₄ and water removal via a Dean-Stark trap with subsequent wash with basic solution (sodium bicarbonate), then purified by distillation: ¹H NMR (400 MHz, CDCl₃) δ 0.86-1.76 (m, 13H), 4.31 (m, 2H), 7.58 (d, J=8 Hz, 2H), 7.91 (d, J=8.0 Hz, 2H). Hexyl 3-bromobenzoate was prepared from the condensation of 3-bromobenzoic acid and OXO-C₆ alcohols by refluxing in benzene with water removal via a Dean-Stark trap, then purified by distillation: ¹H NMR (400 MHz, CDCl₃) δ 0.91-1.77 (m, 11H), 4.34 (m, 2H), 7.31 (m, 2H), 7.64 (m, 1H), 7.77 (d, J=8.0 Hz, 1H). Hexyl 4-bromobenzoate (1 equiv), bispinacolatodiboron (1.1 equiv) and potassium acetate (3 equiv) were dissolved in DMF to make a 0.25 M solution with respect to the bromobenzoic ester. The mixture was degassed with N₂ and palladium diacetate (0.02 equiv) was added. The reaction was heated between 80-90° C. until completion (approx. 5 h), then cooled. Water was added and the mixture extracted 3 times with ethyl acetate. The combined organic layers were washed twice with water and twice with brine, then dried (MgSO₄), filtered and concentrated under reduced pressure. The unpurified grayish yellow oil was then transferred to a 3-neck flask and dissolved in toluene to make a 0.2 M solution. An equivalent of a hexyl 3-bromobenzoate and a 2 M solution of potassium carbonate (5 equiv) was added and the mixture degassed. Palladium tetrakistriphenylphosphine (0.01 equiv) was added and the reaction heated at reflux overnight. After cooling, the aqueous layer was extracted with ethyl acetate and combined organic layers washed twice with water and twice with brine. It was then dried (MgSO₄), filtered and concentrated. The crude oil was purified by passage through a short silica gel column (eluting with 10:90 ethyl acetate:hexanes) followed by vacuum distillation: ¹H NMR (400 MHz, CDCl₃) δ 0.90-1.79 (m, 25H), 4.32 (m, 2H), 7.52 (t, J=8.0 Hz, 1H), 7.67 (d, J=8.0 Hz, 2H), 7.77 (m, 1H), 8.03 (m, 1H), 8.11 (m, 2H), 8.28 (s, 1H); ¹³C NMR (100 MHz, CDCl₃) 11.4-35.9 (10C), 63.69, 65.4, 127.2 (2C), 128.5, 129.2, 129.3, 129.9, 130.3 (2C), 131.5, 131.6, 140.5, 144.6, 166.6 (2C).

Example 24: Preparation of 2,3'-biphenyldicarboxylate using OXO-C₆ alcohols

Hexyl 2-bromobenzoate was prepared from the condensation of 2-bromobenzoic acid and OXO-C₆ alcohols by refluxing in benzene with H₂SO₄ and water removal via a Dean-Stark trap with subsequent wash with basic solution (sodium bicarbonate), then purified by distillation: ¹H NMR (400 MHz, CDCl₃) δ 0.91-1.77 (m, 11H), 4.34 (m, 2H), 7.31 (m, 2H), 7.64 (d, J=8.0 Hz, 1H), 7.77 (d, J=8.0 Hz, 1H). Hexyl 3-bromobenzoate (1 equiv), bispinacolatodiboron (1.1 equiv) and potassium acetate (3 equiv) were dissolved in DMF to make a 0.25 M solution with respect to the bromobenzoic ester. The mixture was degassed with $N_2$ and palladium diacetate (0.02 equiv) was added. The reaction was heated between 80-90° C. until completion (approx. 5 h), then cooled. Water was added and the mixture extracted 3 times with ethyl acetate. The combined organic layers were washed twice with water and twice with brine, then dried ($MgSO_4$), filtered and concentrated under reduced pressure. The unpurified grayish yellow oil was then transferred to a 3-neck flask and dissolved in toluene to make a 0.2 M solution. An equivalent of a hexyl 2-bromobenzoate and a 2 M solution of potassium carbonate (5 equiv) was added and the mixture degassed. Palladium tetrakistriphenylphosphine (0.01 equiv) was added and the reaction heated at reflux overnight. After cooling, the aqueous layer was extracted with ethyl acetate and combined organic layers washed twice with water and twice with brine. It was then dried ($MgSO_4$), filtered and concentrated. The crude oil was purified by passage through a short silica gel column (eluting with 10:90 ethyl acetate:hexanes) followed by vacuum distillation: $^1H$ NMR (400 MHz, $CDCl_3$) δ 0.81-1.77 (m, 25H), 4.04 (m, 2H), 4.33 (m, 2H), 7.46 (m, 1H), 7.50 (m, 4H), 7.89 (m, 1H), 8.03 (m, 2H); $^{13}C$ NMR (100 MHz, $CDCl_3$) 14.9-35.4 (10C), 63.7, 65.4, 127.8, 128.2, 128.5, 129.6, 130.3, 130.7, 130.9, 131.2, 131.5, 133.0, 141.7, 142.1, 166.6, 168.6.

Table 2 summarizes the conditions for forming different esters.

The structures of the samples listed in the above table are shown below:

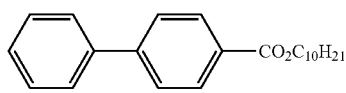

Example 1

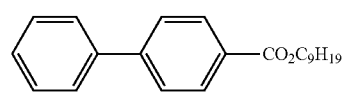

Example 2

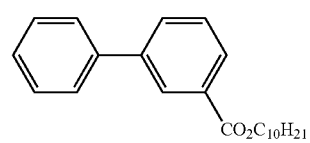

Example 3

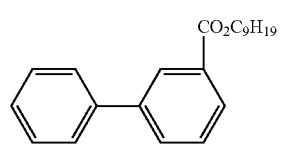

Example 4

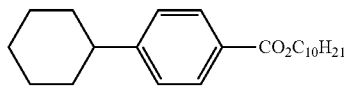

Example 6

TABLE 2

| Example # | Acid | Alcohol | Temp (° C.) | Purity, % by GC |
|---|---|---|---|---|
| 1 | 4-phenyl benzoic acid | OXO-$C_{10}$ | 208-220 | 99.5 |
| 2 | 4-phenyl benzoic acid | OXO-$C_9$ | 185-220 | 99.5 |
| 3 | 3-phenyl benzoic acid | OXO-$C_{10}$ | 175-183 | 99.2 |
| 4 | 2-phenyl benzoic acid | OXO-$C_9$ | 205-208 | 99.6 |
| 5 | Blend of examples 1, 3 and 4 | | | |
| 6 | 4-cyclohexylbenzoic acid | OXO-$C_{10}$ | 217-220 | 99.2 |
| 7a | blend of biphenyl-4-carboxylic acid (70%) plus 4-cyclohexylbenzoic acid (30%), 2'-methylbiphenyl-3-carboxylic acid | OXO-$C_{10}$ | 145-182 | 99.42 |
| 7b | blend of biphenyl-4-carboxylic acid (70%) plus 4-cyclohexylbenzoic acid (30%), | OXO-$C_{10}$ | 208-220 | 99.6 |
| 7c | blend of biphenyl-4-carboxylic acid (50%) plus 4-cyclohexylbenzoic acid (50%), | OXO-$C_{10}$ | 208-220 | 99.6 |
| 7d | blend of biphenyl-4-carboxylic acid (30%) plus 4-cyclohexylbenzoic acid (70%), | OXO-$C_{10}$ | 208-220 | 99.6 |
| 8 | 4'-methylbiphenyl-4-carboxylic acid | OXO-$C_9$ | 184-185 | 99.6 |
| 9 | 4'-methylbiphenyl-2-carboxylic acid | OXO-$C_9$ | 145-162 | 99.86 |
| 10 | 2'-methylbiphenyl-3-carboxylic acid | OXO-$C_{10}$ | 175-182 | 99.42 |
| 11 | 4'-methylbiphenyl-3-carboxylic acid | OXO-$C_{10}$ | | |
| 12 | 2'-methyl-3-biphenylcarboxylic acid | OXO-$C_{10}$ | | |
| 13 | 3'-methyl-4-biphenylcarboxylic acid | OXO-$C_{10}$ | | |
| 14 | 3'-methyl-4-biphenylcarboxylic acid | OXO-$C_9$ | | |
| 15 | 3'-methyl-2-biphenylcarboxylic acid | OXO-$C_{10}$ | | |
| 16 | 3'-methyl-3-biphenylcarboxylic acid | OXO-$C_{10}$ | | |
| 17 | blend of examples 8, 9, &10 | OXO-$C_9$ + OXO-$C_{10}$ | NA | NA |
| 18 | biphenyl-2,2'-dicarboxylic acid | $C_5$ (65/35) n-pentanol/2-methylpentanol | 174-184 | 99.1 |
| 19 | biphenyl-2,2'-dicarboxylic acid | $C_6$ (65/35) n-hexanol/2-methylpentanol | 189-191 | 97.9 |
| 20 | biphenyl-2,2'-dicarboxylic acid | OXO-$C_9$ | 206-215 | 99.4 |
| 21 | biphenyl-4,4'-dicarboxylic acid | Linear $C_6$ alcohol | | |
| 22 | biphenyl-4,4'-dicarboxylic acid | OXO-$C_6$ | | |
| 23 | biphenyl-3,4'-dicarboxylic acid | OXO-$C_6$ | | |
| 24 | biphenyl-2,3'-dicarboxylic acid | OXO-$C_6$ | | |

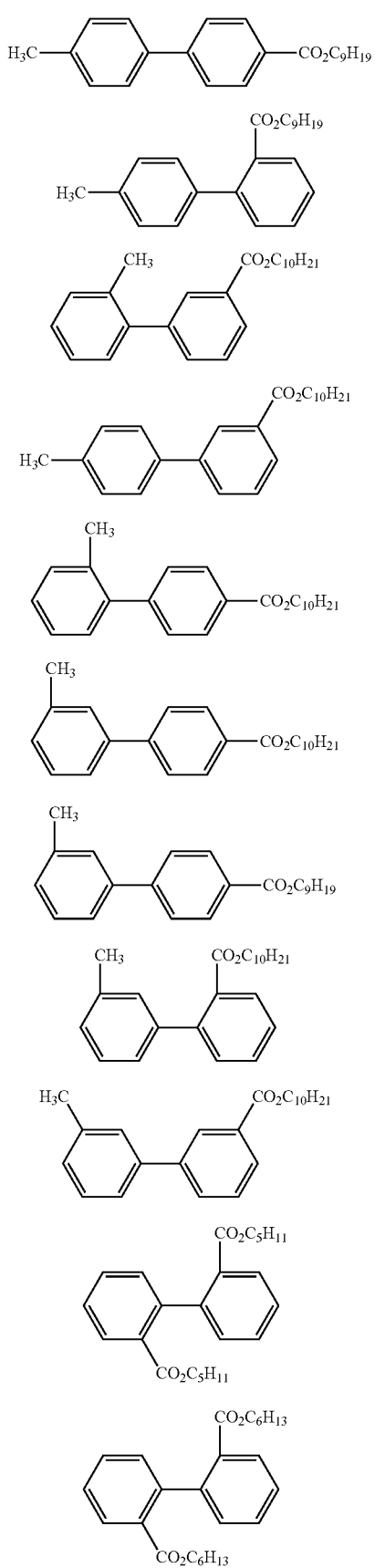

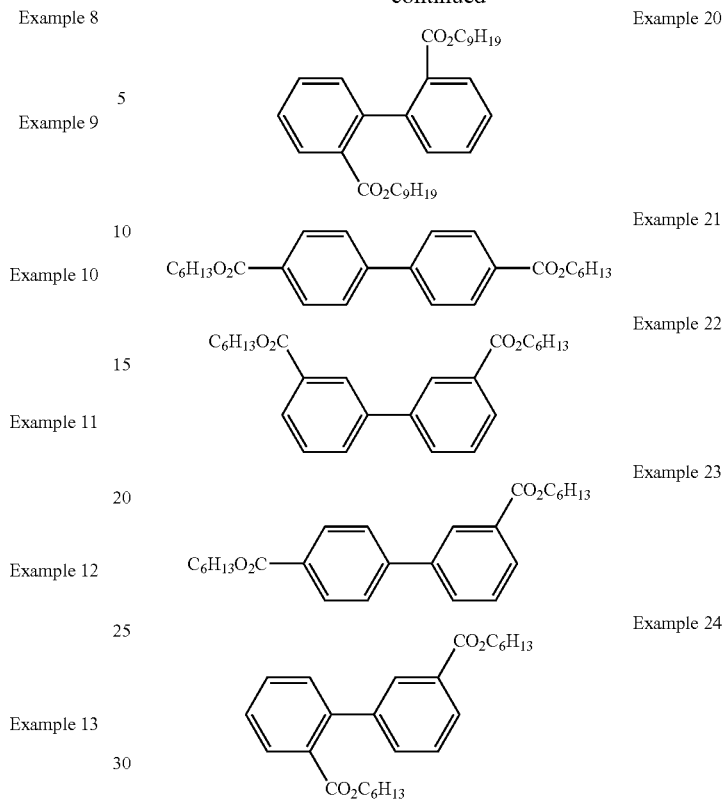

Method for Preparation of Plasticized Polymer Testing Bars by Solvent Method A:

A 5.85 g portion of the ester sample (or comparative commercial plasticizer DINP) was weighed into an Erlenmeyer flask which had previously been rinsed with uninhibited tetrahydrofuran (THF) to remove dust. A 0.82 g portion of a 70:30 by weight solid mixture of powdered Drapex™ 6.8 (Crompton Corp.) and Mark™ 4716 (Chemtura USA Corp.) stabilizers was added along with a stirbar. The solids were dissolved in 117 mL uninhibited THF. Oxy Vinyls™ 240 F PVC (11.7 g) was added in powdered form and the contents of the flask were stirred overnight at room temperature until dissolution of the PVC was complete. The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, pre-heated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™- coated aluminum foil and the following multistage press procedure was used at 170° C. with no release between stages: (1) 3 minutes with 1-2 ton overpressure; (2) 1 minute at 10 tons; (3) 1 minute at 20 tons; (4) 1 minute at 30 tons; (5) 3 additional minutes at 30 tons; (6) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness or exudation after pressing unless otherwise noted. The bars were allowed to age at room temperature for at least 1 week prior to evaluation of phase behavior with Differential Scanning calorimetry (DSC) and thermo-physical properties with Dynamic Mechanical Thermal Analysis (DMTA).

Method for Preparation of Plasticized Polymer Testing Bars by Melt Mixing Method B:

In a 250 ml beaker was added 2.7 g of an additive package containing a 70/30 wt/wt of Paraplex G62 ESO/Mark 4716. To this was added 19.1 g of plasticizer and the mixture was stirred with a spatula until blended. After blending, 38.2 g of PVC was added and the mixture was mixed forming a paste. The mixture was added to the melt mixture. A Haake Rheomix 600 mixer manufactured by Haake PolyLab System was preheated to the desired mixing temperature (165° C. for most experiments). A coarsely mixed sample consisting of plasticizer, polyvinylchloride and stabilizers was added to the mixer while stirring at 35 rpm. After addition the mixer was stopped for one minute. The mixer was started again and the sample was mixed for five minutes. After mixing for five minutes the mixer was stopped and disassembled. The mixed sample was removed hot.

Bars were made using a Carver press according to the following procedure: The press was preheated with the mold at 170° C. The mold was removed hot and the plasticized PVC was placed on the mold. The mold was put back into the press and remained there for 3 minutes without pressure. Then 10 tons of pressure was placed on the mold and remained for 1 minute, the pressure was increased to 15 tons and remained there for another minute. Finally, the pressure was increased to 30 tons and remained at that pressure for 3 minutes. The pressure was released after 3 minutes, then the mold was placed in the cold side of the press and 30 tons of pressure was added for another 3 minutes. Most of the analytical testing was done one week after pressing.

98° C. Weight Loss Comparison of PVC Bars Plasticized with Esters Versus PVC Bars Plasticized with Commercial Plasticizer:

Two each of the PVC sample bars prepared above were placed separately in aluminum weighing pans and placed inside a convection oven at 98° C. Initial weight measurements of the hot bars and measurements taken at specified time intervals were recorded and results were averaged between the bars. The averaged results are shown in Table 5.

70° C. Humid Aging Clarity Comparison of PVC Bars Plasticized with Esters Versus PVC Bars Plasticized with Commercial Plasticizer:

Using a standard one-hole office paper hole punch, holes were punched in two each of the sample bars prepared above ⅛" from one end of the bar. The bars were hung in a glass pint jar (2 bars per jar) fitted with a copper insert providing a stand and hook. The jar was filled with ~½" of distilled water and the copper insert was adjusted so that the bottom of each bar was ~1" above the water level. The jar was sealed, placed in a 70° C. convection oven, and further sealed by winding Teflon™ tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for 14 days (until reversible humidity-induced opacity had disappeared). The bars were evaluated visually for clarity. All bars exhibited complete opacity during the duration of the test and for several days after removal from the oven. Notes on 70° C. Humid Aging Clarity and appearance properties of ester- and DINP-containing PVC bars are shown in Table 5A.

Differential Scanning Calorimetry (DSC) and Thermogravimetric Analysis (TGA) Property Study of Esters and Plasticized Bars:

Thermogravimetric Analysis (TGA) was conducted on the neat esters using a TA Instruments TGA5000 instrument (25-450° C., 10° C./min, under 25 cc $N_2$/min flow through furnace and 10 cc $N_2$/min flow through balance; sample size approximately 10 mg). Table 4 provides comparisons of volatilities and glass transitions (Tg) of the different ester fractions. Tg's given in Table 4 are midpoints of the second heats obtained by Differential Scanning calorimetry (DSC) using a TA Instruments Q2000 calorimeter fitted with a liquid $N_2$ cooling accessory. Samples were loaded at room temperature and cooled to −130° C. at 10° C./min and analyzed on heating to 75° C. at a rate of 10° C./min Table 5 provides a volatility comparison of the neat and plasticized PVC bars.

TABLE 4

| Example | TGA 1% Wt Loss (° C.) | TGA 5% Wt Loss (° C.) | TGA 10% Wt Loss (° C.) | TGA Wt Loss at 220° C. (%) | DSC $T_g$ (° C.) |
| --- | --- | --- | --- | --- | --- |
| 1 | 182.5 | 214.3 | 231.9 | 6.3 | −64.7 |
| 2 | 177.3 | 207 | 221.9 | 9.2 | −64.1 |
| 3 | 171.1 | 200.1 | 215.3 | 12.2 | −66.7 |
| 4 | 150.5 | 179.8 | 194.5 | 28.1 | −66.3 |
| 5 | 161.5 | 191.8 | 207.6 | 16.5 | −66.3 |
| 6 | 167.7 | 199.0 | 215.1 | 12.2 | −75.2 |
| 7a | 170.8 | 200.3 | 216.4 | 11.5 | −68.0 |
| 7b | 176.2 | 206.0 | 221.1 | 9.5 | −69.2 |
| 7c | 173.3 | 203.0 | 217.9 | 11.0 | −71.3 |
| 7d | 172.5 | 201.6 | 216.3 | 11.8 | −73.2 |
| 8 | 183.7 | 219.2 | 235.3 | 5.2 | −80.6 |
| 9 | 173.9 | 204.8 | 220.2 | 9.9 | −73.6 |
| 10 | 171.8 | 203.7 | 219.9 | 10.1 | −65.9 |
| 11 | 188.6 | 219.4 | 235.3 | 5.1 | −63.2 |
| 12 | 187.9 | 214.1 | 229.8 | 6.6 | −63.9 |
| 13 | 192.1 | 222.9 | 238.7 | 4.4 | −65.9 |
| 14 | 185.3 | 216.4 | 232.1 | 5.9 | −64.1 |
| 15 | 148.6 | 180.9 | 196.3 | 26.1 | −67.7 |
| 16 | 177.1 | 208.6 | 223.5 | 8.6 | −66.9 |
| 17 | 173.1 | 208.2 | 224.6 | 8.2 | −63.3 |
| 18 | 159.9 | 188.6 | 203.1 | 19.8 | −75.0 |
| 19 | 173.9 | 204.8 | 220.2 | 9.9 | −73.6 |
| 20 | 166.1 | 192.8 | 206.4 | 18.7 | −76.0 |
| 21 | — | — | — | — | — |
| 22 | — | — | — | — | — |
| 23 | 216.06 | 249.13 | 265.1 | 1.195 | −64.0 |
| 24 | — | — | — | — | — |

— Data not taken

TABLE 5

| Plasticizer Used in Bar | TGA 1% Wt Loss (° C.) | TGA 5% Wt Loss (° C.) | TGA 10% Wt Loss (° C.) | TGA % Wt Loss at 220° C. |
| --- | --- | --- | --- | --- |
| None (Neat PVC) | 129.9 | 192.3 | 255.4 | 6.3 |
| 1 | 199.1 | 239.9 | 251.7 | 2.3 |

TABLE 5-continued

| Plasticizer Used in Bar | TGA 1% Wt Loss (° C.) | TGA 5% Wt Loss (° C.) | TGA 10% Wt Loss (° C.) | TGA % Wt Loss at 220° C. |
|---|---|---|---|---|
| 2 | 192.5 | 232.4 | 251.2 | 3.1 |
| 3 | 188.0 | 230.2 | 246.8 | 3.43 |
| 4 | 170.9 | 207.4 | 239.7 | 6.7 |
| 5 | 180.4 | 222.7 | 243.6 | 4.6 |
| 6 | 185.3 | 226.9 | 244.7 | 3.9 |
| 7a | 191.1 | 233.0 | 246.0 | 3.1 |
| 7b | 188.3 | 229.0 | 244.7 | 3.6 |
| 7c | 188.8 | 230.2 | 245.6 | 3.4 |
| 7d | 186.5 | 226.8 | 244.2 | 3.9 |
| 8 | 206.1 | 244.2 | 257.1 | 1.8 |
| 9 | 176.2 | 214.7 | 243.2 | 5.9 |
| 10 | 189.0 | 230.2 | 247.9 | 3.5 |
| 11 | 194.7 | 235.9 | 248.2 | 2.7 |
| 12 | 187.3 | 229.5 | 245.1 | 3.5 |
| 13 | 196.5 | 238.7 | 249.3 | 2.4 |
| 14 | 192.1 | 235.1 | 246.7 | 2.7 |
| 15 | 169.0 | 210.2 | 235.2 | 6.7 |
| 16 | 191.5 | 234.8 | 246.1 | 2.9 |
| 17 | 191.2 | 237.6 | 252.1 | 2.8 |
| 18 | 184.3 | 225.2 | 249.2 | 4.2 |
| 19 | 188.5 | 231.9 | 247.4 | 3.3 |
| 20 | 218.7 | 249.1 | 262.4 | 1.1 |
| 21 | 233.0 | 245.6 | 254.6 | 0.7 |
| 22 | 217.3 | 250.9 | 265.5 | 1.1 |
| 23 | 229.6 | 251.7 | 265.0 | 0.8 |
| 24 | 202.3 | 243.9 | 253.3 | 1.8 |

Demonstration of Plasticization of PVC with Different Esters Made Using this Disclosure Via Differential Scanning Calorimetry (DSC):

Differential Scanning calorimetry (DSC) was performed on the compression-molded sample bars prepared above (PVC:plasticizer ratio=2:1) using a TA Instruments Q2000 calorimeter fitted with a liquid $N_2$ cooling accessory. Samples were loaded at room temperature and cooled to −110° C. at 10° C./min, and then analyzed on heating at a rate of 10° C./min to 130-160° C. for plasticized PVC bars, and to 100° C. for the comparative neat PVC bar. Small portions of the sample bars (typical sample mass 5-7 mg) were cut for analysis, making only vertical cuts perpendicular to the largest surface of the bar to preserve the upper and lower compression molding "skins". The pieces were then placed in the DSC pans so that the upper and lower "skin" surfaces contacted the bottom and top of the pan. Table 6 provides the first heat Tg onset, midpoint, and end for neat PVC and the plasticized bars. A lowering and broadening of the glass transition for neat PVC was observed upon addition of the esters, indicating plasticization and extension of the flexible temperature range of use for neat PVC.

TABLE 5A

Notes on 70° C. Humid Aging Clarity and Appearance of Ester- and DINP-Containing PVC Bars.

| Example No. (Ester Used in Bar) | Notes on Bar |
|---|---|
| DINP[1] | Flex and brownish |
| 1 | Similar to DINP |
| 2 | Very flex and clear |
| 3 | Very flex and colorless |
| 4 | Very flex and yellowish |
| 5 | Very flex and yellowish |
| 6 | Very flex and yellowish |
| 7a | More flex than DINP |
| 7b | More flex than DINP |
| 7c | Much more flex than DINP |
| 7d | Much more flex than DINP |

TABLE 5A-continued

Notes on 70° C. Humid Aging Clarity and Appearance of Ester- and DINP-Containing PVC Bars.

| Example No. (Ester Used in Bar) | Notes on Bar |
|---|---|
| 8 | NA |
| 9 | NA |
| 10 | Stiffer than DINP |
| 11 | NA |
| 12 | NA |
| 13 | NA |
| 14 | NA |
| 15 | Similar to DINP |
| 16 | A bit stiffer than DINP, similar color to DINP |
| 17 | Similar to DINP |
| 18 | Colorless and flex |
| 19 | Similar to DINP |
| 20 | Very stiff |
| 21 | NA |
| 22 | More flex than DINP |
| 23 | Similar to DINP |
| 24 | Similar to DINP |

[1]Bars made following example 44 method A
[2]Bars made following example 44 method B

TABLE 6

| Plasticizer Used in Bar | $T_g$ Onset (° C.) | $T_g$ Midpt (° C.) | $T_g$ End (° C.) | $T_m$ Max (° C.) and $DH_f (J/g)^a$ |
|---|---|---|---|---|
| None (Neat PVC) | 44.5 | 46.4 | 48.9 | not calc. |
| 1 | −35.3 | −12.6 | 10.2 | 61.6, 1.4 |
| 2 | −18.1 | −1.1 | 16.1 | 55.3, 0.9 |
| 3 | −39.5 | −15.6 | 8.1 | 55.2, 1.1 |
| 4 | −42.7 | −18.9 | 4.9 | 60.1, 0.5 |
| 5 | −37.9 | −13.8 | 10.4 | 55.2, 0.9 |
| 6 | −39.0 | −14.0 | 12.5 | 58.2, 0.9 |
| 7a | −32.7 | −10.6 | 11.5 | 54.1, 1.0 |
| 7b | −30.4 | −9.1 | 12.3 | 56.4, 1.1 |
| 7c | −33.3 | −10.6 | 12.4 | 56.3, 1.0 |
| 7d | −36.1 | −13.4 | 10.0 | 55.5, 1.1 |
| 8 | −17.2 | −1.3 | 14.6 | 54.5, 0.3 |
| 9 | −27.0 | −10.6 | 6.0 | 54.7, 86.1 and 0.5, 0.2, respectively |
| 10 | −39.4 | −11.9 | 15.9 | 53.0, 1.1 |
| 11 | −28.5 | −8.0 | 12.7 | 52.3, 1.1 |
| 12 | −65.5, −33.5 | −61.3, −11.1 | −57.0, 11.7 | 55.2, 0.9 |
| 13 | −25.5 | −6.0 | 13.5 | 56.9, 0.9 |
| 14 | −24.6 | −4.6 | 15.4 | 56.0, 1.0 |
| 15 | −36.6 | −13.3 | 10.7 | 54.6, 0.8 |
| 16 | −28.7 | −8.7 | 11.6 | 54.5, 0.8 |
| 17 | −33.8 | −13 | 8.3 | 55.1, 0.9 |
| 18 | −15.9 | −0.5 | 14.8 | 56.2, 0.8 |
| 19 | −19.6 | −3.6 | 12.4 | 56.7, 0.9 |
| 20 | −18.5 | −8.8 | 0.9 | 54.6, 1.1 |
| 21 | −2.5 | 8.2 | 21.2 | — |
| 22 | −31.0 | 10.2 | 10.6 | 53.5, 0.8 |
| 23 | −19.2 | −2.2 | 15.0 | 53.9, 0.8 |
| 24 | −22.9 | −8.2 | 6.9 | 58.2, 1.0 |

— Data not obtained.
$^a$Most sample bars showed a weak melting point ($T_m$) from the crystalline portion of PVC. Often this weak transition was not specifically analyzed, but data is given here in instances where it was recorded.

Demonstration of Plasticization of PVC with Different Esters Via Dynamic Mechanical Thermal Analysis (DMTA):

A TA Instruments DMA Q800 fitted with a liquid $N_2$ cooling accessory and a three-point bend clamp assembly was used to measure the thermo-mechanical performance of neat PVC and the PVC/plasticizer blend sample bars prepared above. Samples were loaded at room temperature and cooled to −90° C. at a cooling rate of 3° C./min After equilibration, a dynamic experiment was performed at one frequency using the following conditions: 3° C./min heating rate, 1 Hz frequency, 20 μm amplitude, 0.01 N pre-load force, force track 120%. Two or three bars of each sample were typically analyzed and numerical data was averaged. The DMTA measurement gives storage modulus (elastic response modulus) and loss modulus (viscous response modulus); the ratio of loss to storage moduli at a given temperature is tan δ (tan delta). The tan δ peak is associated with the glass transition (temperature of the brittle-ductile transition) and is more easily interpreted for plasticized systems compared with the DSC curves. The beginning (onset) of the glass transition, Tg, was obtained from the tan δ curve for each sample by extrapolating a tangent from the steep inflection of the curve and the first deviation of linearity from the baseline prior to the beginning of the peak. Table 7 provides a number of DMTA parameters for neat PVC and PVC bars plasticized with materials described above: Tg onset (taken from tan δ); peak of the tan δ curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material.). The storage modulus at 25° C. provides an indication of plasticizer efficiency (i.e., the amount of plasticizer required to achieve a specific stiffness); the higher the storage modulus, the more plasticizer required. The flexible use temperature range of the plasticized PVC samples is evaluated as the range between the Tg onset and the temperature at which the storage modulus was 100 MPa. A lowering and broadening of the glass transition for PVC is observed upon addition of the esters, indicating plasticization and extension of the flexible temperature range of use for PVC. Plasticization (enhanced flexibility) is also demonstrated by lowering of the PVC room temperature storage modulus upon addition of the esters.

TABLE 7

| Plasticizer Used in Bar | Tan δ $T_g$ Onset (° C.) | Tan δ Peak (° C.) | 25° C. Storage Mod. (MPa) | Temp. of 100 MPa Storage Mod. (° C.) | Flexible Use Range (° C.)$^a$ |
|---|---|---|---|---|---|
| None (Neat PVC) | 44.0 | 61.1 | 1433 | 57.1 | 13.1 |
| 1 | −38.6 | 20.6 | 36.4 | 17.3 | 55.9 |
| 2 | −28.3 | 19 | 35.7 | 17.1 | 45.4 |
| 3 | −40.3 | 14.5 | 35.4 | 14.4 | 54.8 |
| 4 | −34.8 | 20.2 | 48.5 | 19.1 | 53.9 |
| 5 | −37.0 | 16.3 | 26.6 | 13.5 | 50.5 |
| 6 | −50.0 | 26.8 | 59.9 | 20.0 | 70.0 |
| 7a | −34.7 | 23.1 | 35.0 | 16.9 | 51.5 |
| 7b | −38.2 | 20.3 | 42.5 | 16.5 | 54.7 |
| 7c | −42.7 | 19.5 | 58.2 | 18.2 | 60.9 |
| 7d | −43.2 | 23.2 | 49.3 | 18.2 | 61.4 |
| 8 | −20.5 | 23.4 | 52.4 | 20.5 | 41.0 |
| 9 | −31.6 | 17.1 | 38.9 | 16.5 | 48.2 |
| 10 | −45.2 | 23.1 | 49.1 | 18.4 | 63.6 |
| 11 | −33.6 | 21.0 | 31.6 | 16.2 | 49.8 |
| 12 | −40.9 | 27.1 | 66.3 | 21.4 | 62.4 |
| 13 | −32.6 | 19.9 | 38.9 | 16.7 | 49.3 |
| 14 | −27.0 | 20.4 | 38.4 | 16.8 | 43.8 |
| 15 | −40.2 | 18.2 | 34.3 | 13.8 | 54.0 |
| 16 | −38.0 | 17.8 | 34.6 | 14.7 | 52.6 |
| 17 | −24.8 | 20.4 | 45.0 | 18.1 | 42.9 |
| 18 | −26.7 | 21.0 | 37.5 | 17.5 | 44.2 |
| 19 | −24.0 | 17.6 | 42.8 | 17.2 | 41.2 |
| 20 | −28.1 | 24.5 | 61.3 | 20.6 | 48.7 |

TABLE 7-continued

| Plasticizer Used in Bar | Tan δ $T_g$ Onset (° C.) | Tan δ Peak (° C.) | 25° C. Storage Mod. (MPa) | Temp. of 100 MPa Storage Mod. (° C.) | Flexible Use Range (° C.)$^a$ |
|---|---|---|---|---|---|
| 21 | 18.2 | 47.1 | 1588 | 43.6 | 25.5 |
| 22 | −24.9 | 20.7 | 37.4 | 16.7 | 41.6 |
| 23 | −21.3 | 21.9 | 56.9 | 20.1 | 41.4 |
| 24 | −27.4 | 18.9 | 35.8 | 12.0 | 39.4 |

Table 8 summarizes the useful tests for plasticizing performance using esters from Examples 1-10; DINP (diisononylphthalate) is used for comparison.

TABLE 8

| Example No. (Ester Used in Bar) | Viscosity (units) | Tg | Notes on films or bars |
|---|---|---|---|
| DINP$^{(1)}$ | 100 | −79 | |
| 1 | 134 | −64.7 | Flex and colorless similar to DINP |
| 2 | NA | −64.1 | Flex and colorless similar to DINP |
| 3 | 133 | −75.0 | Flex and colorless similar to DINP |
| 4 | NA | −66.3 | Stiffer than DINP |
| 5 | NA | −80.6 | Very flexible |
| 6 | 104 | −60.4 | Flex, a bit darker than DINP |
| 7a | NA | | Similar to DINP |
| 7b | NA | −75.1 | Similar to DINP |
| 7c | NA | −73.6 | Similar to DINP |
| 7d | NA | | Similar to DINP |
| 8 | 161.7 | | NA |
| 9 | NA | | NA |
| 10 | NA | | Similar to DINP |
| 11 | NA | | NA |
| 12 | 225.5 | | NA |
| 13 | 204.1 | | NA |
| 14 | 190.8 | | NA |
| 15 | 105.5 | | Very dark and stiffer than DINP |
| 16 | 228.2 | | More flex than DINP |
| 17 | 165.2 | | Similar to DINP |
| 18 | 86.6 | | Stiffer than DINP |
| 19 | 117.8 | | Similar to DINP |
| 20 | 259.5 | | Stiffer than DINP and exudates |
| 21 | NA | | NA |
| 22 | NA | | Very flex colorless |
| 23 | NA | | Similar to DINP |
| 24 | NA | | More flex than DINP |

Example 25

A PVC plastisol was prepared according the ASTM D1755 method, by mixing in a Hobart mixer 150 grams of the plasticizer of Example 1 the 4-phenyl-benzoic acid isodecyl alcohol ester, 200 grams of PVC resin, and 6 grams of PVC stabilizer Mark 1221 (Ca/Zn stab) and at varying speeds for 10 minutes. The 1 hour plastisol viscosity after mixing was 4410 cP measured at a shear rate of 180 l/s. By comparison a DINP (available from ExxonMobil Chemical) formulation prepared by the same procedure had a 1 hr plastisol viscosity of 2440 cp.

Weight losses after heating of this plastisol for 4 minutes at 200° C. were 0.21% versus 0.22% for a comparative example based on DINP and 0.24% for a comparative example based on DOTP (available from Aldrich). Dynamic mechanical analysis of the plastisol as it was heated to final fusion, gave an initial gelation temperature of 91° C., final gelation temperature of 116° C., and a fusion temperature of 166° C. The comparative example based on DINP has a gelation temperature of 90° C., a final gelation temperature of 128° C. and a fusion temperature of 173° C. Example 1, the 4-phenyl-benzoic acid isodecyl alcohol ester, was found to be faster fusing plasticizers with lower initial and final gelation temperature.

Thin layers (10-15 mils) of the plastisol were fused in a Werner Mathys forced air oven for 3 minutes at 180° C., then combined and molded at 170° C. for 15 minutes into test plaques. Evaluation of the molded test plaques gave a Shore A Hardness of 47, an ultimate tensile strength of 2217 psi, a 100% modulus of 804 psi and an ultimate elongation of 406%. The comparative example based on DINP gave a Shore A Hardness of 49, an ultimate tensile strength of 2211 psi, a 100% modulus of 777 psi and an ultimate elongation of 416%. The comparative example based on DOTP gave a Shore A Hardness of 49, an ultimate tensile strength of 2209 psi, a 100% modulus of 809 psi and an ultimate elongation of 411%. Shore A Hardness was determined by ASTM D 2240-86. Tensile properties (including ultimate tensile strength, ultimate elongation) were determined by ASTM D 638 (30 mil test specimens, Type C die). Mechanical properties (including 100% modulus) were determined by ASTM D 638.

Example 26

The plasticizer from Example 1, the 4-phenyl-benzoic acid isodecyl alcohol ester, was tested as plasticizer in flexible polyvinyl chloride and compared to DINP available from ExxonMobil Chemical Company and DOTP available from Aldrich. All plasticizers were tested at the same concentrations. All formulations were prepared at the same plasticizer pph (parts per hundred parts of PVC) level. A solution was prepared by dissolving 0.5 grams of stearic acid with slight heating and stirring in 120 grams of the plasticizer from Example 1. After the stearic acid dissolved, the solution was cooled to room temperature, and 6.0 grams of the PVC stabilizer Mark™ 1221 (Ferro) was added. This solution was then added to 200 grams of PVC resin (OXY™ 240F) and mixed under low speed in a Hobart mixer. The mixture was processed into a flexible PVC product through milling on a Dr. Collins roll mill, at 165° C. for 6 minutes. The milled sheet was removed from the roll mill, cooled to room temperature, and then portions of this product were pressed to test specimens of various thicknesses, at 170° C. for 15 minutes. After cooling, the test specimens were removed from the molds, and conditioned for 7 days at 22° C. and 50% relative humidity. The Shore A hardness (ASTM D 2240-86) and tensile properties (30 mil test specimens, Type C die) were measured and are reported in Table 26.

The mechanical properties (original) were obtained from samples in a Zwick tensile tester (T1-FR005TN.A50) measuring the modulus at 100% extension, the ultimate tensile strength in psi and ultimate elongation in % according to ASTM D 638. The same mechanical properties were measured on dumbbells that had been aged at 100° C. for 7 days, 100° C., with airflow of 150 air changes/hr. Retained tensile strength was 101% of the original tensile and elongation at break was 76% of the original elongation at break.

The low temperature flexibility of the materials was measured using the Clash and Berg test (ASTM D1043-84) gave a temperature of −15° C.

TABLE 26

| | DINP 60 phr | DOTP 60 phr | Plasticizer from Example 1 60 phr |
|---|---|---|---|
| Oxy™ 240 | 100 | 100 | 100 |
| Mark™ 1221 (Ca/Zn Stab.) | 3.3 | 3.3 | 3.3 |
| ESO (epoxidized soybean oil) | 2.20 | 2.20 | 2.2 |
| Stearic Acid | 0.3 | 0.3 | 0.3 |
| Original Mechanical Properties | | | |
| Shore A Hardness (15 sec.) | 68 | 68 | 68 |
| 100% Modulus Strength, psi | 1252 | 1304 | 1381 |
| Ultimate Tensile Strength, psi | 2695 | 2769 | 2927 |
| Ultimate Elongation, % | 403 | 385 | 355 |
| Retained Properties after ageing for 10 days at 100° C. forced ventilation | | | |
| Retained 100% Modulus Strength, % | 132 | 135 | 170 |
| Retained Tensile Strength, % | 106 | 103 | 101 |
| Retained Elongation, % | 91 | 92 | 76 |
| Carbon Volatility (24 hours at 70 C.) | | | |
| Mean (3 specimens) | 0.6 | 0.7 | 0.7 |
| Low Temperature | | | |
| Clash Berg (Tf), ° C. | −24 | −32 | −15 |

Example 27: Esterification of 4-phenyl-benzoic acid

Into a five-necked, 2000 ml round bottom flask equipped with a mechanical stirrer, nitrogen inductor, thermometer, Dean-Stark trap and chilled water cooled condenser were added 2 moles of 4-phenyl-benzoic acid (Acros™) and 2.5 moles of respectively Isodecyl alcohol (Exxal™ 10), of Isoundecyl alcohol (Exxal™ 11), of Isotridecyl alcohol (Exxal™ 13). The Dean-Stark trap was filled with alcohol. The alcohol was heated at 100° C. under nitrogen and then degassed several times to remove remaining air. The acid was added in several steps (3) under vigorous stirring. The solution was heated until 180° C. and the catalyst (1% TIOT (toira-isooctyl titanates) on acid) mixed with 20 gr of alcohol was slowly added. The vacuum was at 600 mm Hg. The addition of the catalyst solution took approx. 30 minutes. The temperature was progressively increased to 210-215° C. and the vacuum was reduced to collect the water. When, the theoretical amount of water was collected (approximately), the acid conversion was measured by titration. The vacuum was further decreased (200 mm Hg) in order to collect the excess alcohol (for about one hour).

The mixture was cooled to 90° C. and a solution of $Na_2CO_3$ was added to hydrolyze and/or neutralize catalyst residues and/or neutralize any residual monoester. The ester was filtered via a suction filter with paper filter and filter aid. Steam stripping was done at 160° C. by passing steam (220° C.) through the ester to remove excess alcohol for 1.5 hours at reduced pressure. The product was then dried with nitrogen (30 min) The ester was filtered at room temperature via a suction filter with paper filter and filter aid (Perlite).

Neat properties of the three esters of example 27 are shown in the Table below and are compared to DINP.

Solution temperature of plasticizers is defined as the temperature at which a set amount of PVC gets dissolved in a set amount of plasticizer. The solution temperature is not only influenced by the plasticizer type but also by the PVC resin type and in particular the K Value (DIN 53408 Testing of Plastics; Determination of Solubility Temperature of Polyvinyl Chloride (PVC) in Plasticizers (1967.06.01)).

The solution temperature of the three plasticizers of example 27 were compared with those of DINP and summarized in the table below. Esters of the invention made with C10 and C11 alcohols exhibit lower solution T° than DINP.

Neat plasticizers volatility at elevated temperatures in a forced ventilated oven were assessed (based on ASTM D 2288-97). 10 g neat plasticizer sample was poured into a cup (internal diameter 50 mm, thickness 0.18±0.02 mm and 35 mm height) and placed for 24 hours at 155° C. in a forced ventilated oven (Heraeus oven type UT 6050 UL over 160 air renewal per hour). After 24 hours, the cups were cooled down in a desiccator and the plasticizer loss by evaporation was weighed.

Results are listed in the table below and indicate that all 4-phenyl-benzoic acid esters of example 27 exhibit lower neat volatility than the comparative example DINP.

TABLE 27

| | Esters | | | |
|---|---|---|---|---|
| | DINP | 4-phenyl-benzoic acid ester | 4-phenyl-benzoic acid ester | 4-phenyl-benzoic acid ester |
| Alcohols | | Exxal ™ 10 | Exxal ™ 11 | Exxal ™ 13 |
| Viscosity (mPas) - ASTM D445 | 96 | 127.9 | 158.7 | 262.1 |
| Density (g/cm$^3$) - ASTM D4052 | 0.972 | 1.007 | 1.001 | 0.990 |
| Solution temperature (in ° C.) | 127 | 120 | 124 | 135 |
| Neat plasticizer volatility at 155° C.-24 h - forced ventilation (in wt %) | 7.3 | 5.9 | 5 | 3.8 |

Example 28

PVC plastisols were prepared by mixing in a Hobart mixer. The plastisols were prepared with 100 parts PVC (Solvin 382 NG), 60 parts of ester according to example 27, and 1 part of a conventional stabilizer. The gelation temperatures of the plastisols were determined by an Anton Paar Physica Rheometer MCR 301. The instrument was used in oscillation mode, frequency 1 hz, amplitude 0.01% and the heating rate was 10° C./min Dynamic mechanical analysis of the plastisols as they were heated to final fusion, gave an initial gelation temperature of 103° C. (G' (Elastic modulus) is equal to $10^5$ Pa) for the 4-phenyl-benzoic acid isodecyl alcohol ester, an initial gelation temperature of 116° C. for the 4-phenyl-benzoic acid isoundecyl alcohol ester and an initial gelation temperature of 136° C. for the 4-phenyl-benzoic acid isotridecyl alcohol ester. The comparative example, based on DINP had an initial gelation temperature of 133° C. The 4-phenyl-benzoic acid isodecyl and isoundecyl alcohol esters were found to exhibit lower gelation T° and were faster fusing than DINP as shown on the DMA graph (FIG. 1). Note that in FIG. 1, elastic modulus is plotted as a function of the heating temperature (heating rate is 10° C./min) The top line is the plasticizer derived from the $C_{10}$ alcohol, the second to the top line is the plasticizer derived from the $C_{11}$ alcohol, the third to the top line is DINP, and the bottom line is the plasticizer derived from the $C_{13}$ alcohol.

Example 29: Esterification of 4,4'-biphenyl dicarboxylic acid with OXO-$C_9$ alcohol Into a five-necked, 2000 ml round bottom flask equipped with a mechanical stirrer, nitrogen inductor, thermometer, Dean-Stark trap and chilled water cooled condenser were added 1.2 moles of 4,4'biphenyl dicarboxylic acid (Apollo) and 4.8 moles of Isononyl alcohol (Exxal™ 9). The Dean-Stark trap was filled with alcohol. The alcohol was heated at 100° C. under nitrogen and then degassed several times to remove remaining air. The acid was added in several steps (3) under vigorous stirring. The solution was heated until 180° C. and the catalyst (1% TIOT on acid) mixed with 20 gr of alcohol was slowly added. The vacuum was at 600 mm Hg. The addition of the catalyst solution took approx. 30 minutes. The temperature was progressively increased to 210-220° C. and the vacuum was reduced to collect the water. When the theoretical amount of water was collected, the acid conversion was measured by titration.

The vacuum was further decreased (200 mm Hg) in order to collect excess alcohol (for about one hour). The mixture was cooled to 90° C. and a solution of $Na_2CO_3$ was added to hydrolyze and/or neutralize catalyst residues and/or neutralize any residual monoester. The ester was filtered via a suction filter with paper filter and filter aid. Steam stripping was done at 160° C. by passing steam (220° C.) through the ester to remove excess alcohol during for 1.5 hours at reduced pressure. The product was then dried with nitrogen (30 min). The ester was filtered at room temperature via a suction filter with paper filter and filter aid (Perlite).

Example 29A

Figure 2:
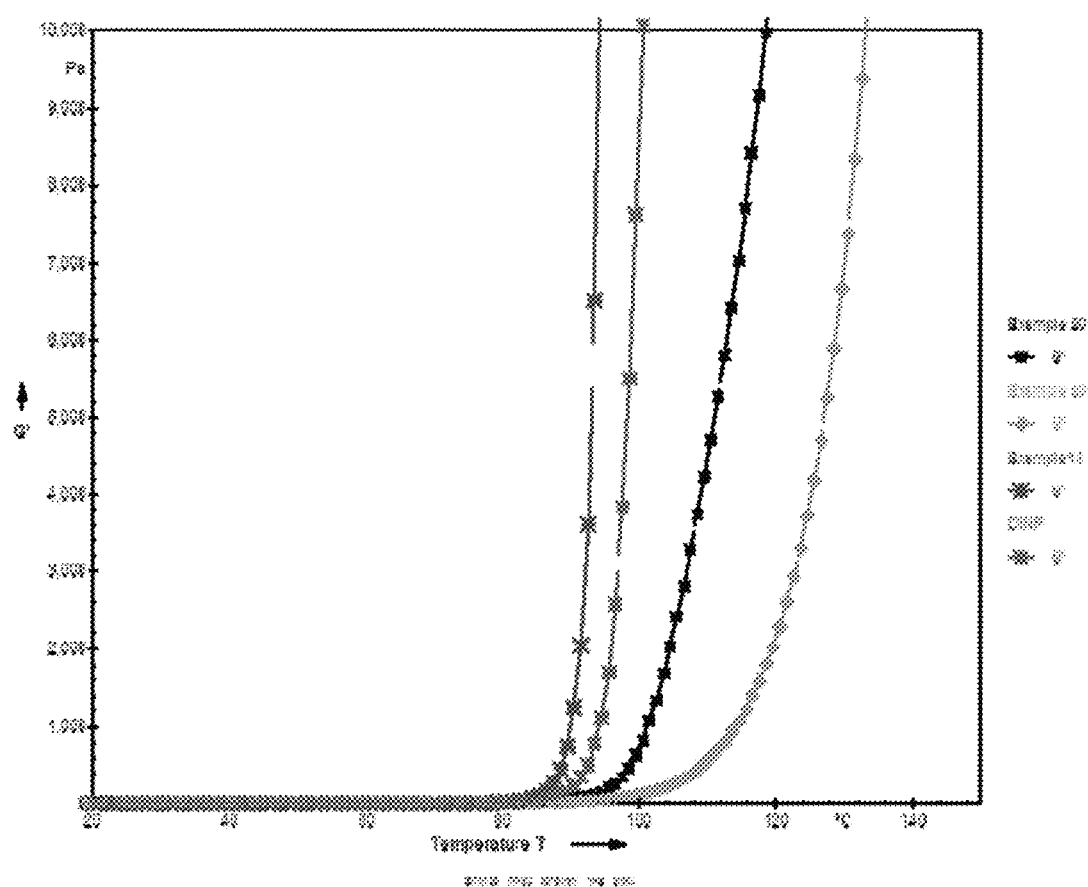
FIG. 2 is a graphed elastic modulus plotted as a function of heating temperature for Example 29A.

PVC plastisols were prepared by mixing in a Hobart mixer. The plastisols were prepared with 100 parts PVC (Solvin 382 NG), 60 parts of the ester prepared according to examples 14, 20 and 29, respectively, and 1 part of a conventional stabilizer. The gelation temperatures of the plastisols were determined by an Anton Paar Physica Rheometer MCR 301. The instrument was used in oscillation mode, frequency 1 hz, amplitude 0.01% and the heating rate was 10° C./min Dynamic mechanical analysis of plastisols is shown in FIG. 2. The evolution of the Elastic modulus G' is plotted for each alcohol ester, in the range of temperature between 80° C. and 140° C. The comparative example was based on DINP (available from ExxonMobil). Note that in FIG. 2, elastic modulus is plotted as a function of the heating temperature (heating rate is 10° C./min) The far left line is the plasticizer derived from example 14, the second to the far left line is DINP, the third to the far left line is the plasticizer derived from example 20, and the right line is the plasticizer derived from example 29.

The 3'methyl-4-biphenyl carboxylic acid ester of $C_9$ alcohol (example 14) shows faster gelling (means G' sudden increase occurs at a lower T°) than DINP while the 2,2'-biphenyl carboxylic acid ester of $C_9$ alcohols (example 20) and the 4,4'-biphenyl carboxylic acid ester of $C_9$ alcohols (example 28) are slower.

Example 30

The following example demonstrates a sample that was prepared by using toluene hydroalkylation/dehydrogenation, then oxidation to make a monoacid, which was esterified with a $C_{10}$ OXO-alcohol.

Example 30A

Synthesis of 0.3% Pd/MCM-49 Catalyst for Toluene Hydroalkylation 80 parts MCM-49 zeolite crystals were combined with 20 parts pseudoboehmite alumina, on a calcined dry weight basis. The MCM-49 and pseudoboehmite alumina dry powder were placed in a Muller mixer and mixed for about 10 to 30 minutes. Sufficient water and 0.05% polyvinyl alcohol was added to the MCM-49 and alumina during the mixing process to produce an extrudable paste. The extrudable paste was formed into a 1/20 inch (0.13 cm) quadrulobe extrudate using an extruder and the resulting extrudate was dried at a temperature ranging from 250° F. to 325° F. (120° C. to 163° C.). After drying, the extrudate was heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution two times. The ammonium nitrate exchanged extrudate was then washed with deionized water to remove residual nitrate prior to calcination in air. The exchanged and dried extrudate was then calcined in a nitrogen/air mixture to a temperature 1000° F. (538° C.). Afterwards, the calcined extrudate was cooled to room temperature. The 80% MCM-49, 20% $Al_2O_3$ extrudate was incipient wetness impregnated with a palladium (II) chloride solution (target: 0.30% Pd) and then dried overnight at 121° C. The dried catalyst was calcined in air at the following conditions: 5 volumes air per volume catalyst per minute, ramp from ambient to 538° C. at 1° C./min and hold for 3 hours.

Example 30B: Toluene Hydroalkylation

The catalyst described above in example 30A was employed to hydroalkylate toluene in a fixed bed reactor as described below. The reactor comprised a stainless steel tube having an outside diameter of: 3/8 inch (0.95 cm), a length of 20.5 inch (52 cm) and a wall thickness of 0.35 inch (0.9 cm). A piece of stainless steel tubing having a length of 8 3/4 inch (22 cm) and an outside diameter of: 3/8 inch (0.95 cm) and a similar length of 1/4 inch (0.6 cm) tubing of were used in the bottom of the reactor (one inside of the other) as a spacer to position and support the catalyst in the isothermal zone of the furnace. A 1/4 inch (0.6 cm) plug of glass wool was placed on top of the spacer to keep the catalyst in place. A 1/8 inch (0.3 cm) stainless steel thermo-well was placed in the catalyst bed to monitor temperature throughout the catalyst bed using a movable thermocouple.

The catalyst was sized to 20/40 sieve mesh or cut to 1:1 length to diameter ratio, dispersed with quartz chips (20/40 mesh) then loaded into the reactor from the top to a volume of 5.5 cc. The catalyst bed was approx. 15 cm in length. The remaining void space at the top of the reactor was filled with quartz chips, with a 1/4 plug of glass wool placed on top of the catalyst bed being used to separate quartz chips from the catalyst. The reactor was installed in a furnace with the catalyst bed in the middle of the furnace at a pre-marked isothermal zone. The reactor was then pressure and leak tested (at approx. 300 psig (2170 kPa)).

The catalyst was pre-conditioned in situ by heating to 25° C. to 240° C. with $H_2$ flow at 100 cc/min and holding for 12 hours. A 500 cc ISCO syringe pump was used to introduce a chemical grade toluene feed to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure at approx. 150 psig (1135 kPa). GC analyses were taken to verify feed composition. The feed was then pumped through the catalyst bed held at the reaction temperature of 120° C. to 180° C. at a WHSV of 2, hydrogen:hydrocarbon mole ratio of 2:1 and a pressure of 15-200 psig (204-1480 kPa).

The liquid products exiting the reactor flowed through heated lines were routed to two collection pots in series, the first pot being heated to 60° C. and the second pot cooled with chilled coolant to about 10° C. Material balances were taken at 12 to 24 hour intervals. Samples were taken and diluted with 50% ethanol for analysis. An Agilent 7890 gas chromatograph with FID detector was used for the analysis. The non-condensable gas products were routed to an on line HP 5890 GC.

The product analysis done on the Agilent 7890 GC was performed with 150 vial sample tray using the following procedure/conditions: 1) Inlet Temp of 220° C.; 2) Detector Temp of 240° C. (Col+make up=constant); 3) Temp Program of initial temp 120° C. hold for 15 min., ramp at 2° C./min to 180° C., hold 15 min; ramp at 3° C./min to 220° C. and hold till end; 4) Column Flow of 2.25 ml/min (27 cm/sec); 5) Split mode, Split ratio 100:1; 6) injector: Auto sampler (0.2 µl); 7). Column Parameters were: Two columns joined to make 120 Meters (coupled with Agilent ultimate union, deactivated; Column # Front end—Supelco β-Dex 120: 60 m×0.25 mm×0.25 µm film joined to Column #2 back end: γ—Dex 325: 60 m×0.25 mm×0.25 µm film.

Example 30C: Synthesis of 1% Pt/0.15% $Sn/SiO_2$ Catalysts for Dehydrogenation

The catalyst was prepared by incipient wetness impregnation. In each case, a 1/20" quadralobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. Each of the resultant products was calcined in air at 350° C. for 3 hours before being used in subsequent catalyst testing.

Example 30D: Dehydrogenation

The hydroalkylation product described above (feed composition: 9% methylcyclohexane, 66% Toluene, 24% methylcyclohexyl toluene, 0.5% dialkylate) was fed to a dehydrogenation unit containing the 1% Pt/0.15% Sn/RT-235 catalyst prepared above in example 30C. The reactor used in these experiments consists of a stainless steel tube. The Standard Reactor is piping with dimensions: 3/8 in×20.5 in×0.35 in wall thickness. A piece of stainless steel tubing 8 3/4 in. long×3/8 in. o.d. and a piece of 1/4 inch tubing of similar length was used in the bottom of the reactor as a spacer (one inside of the other) to position and support the catalyst in the isothermal zone of the furnace. A 1/4 inch plug of glass wool was placed at the top of the spacer to keep the catalyst in place. A 1/8 inch stainless steel thermo-well was placed in the cat bed, long enough to monitor temperature throughout the catalyst bed using a movable thermocouple. The catalyst is loaded with a spacer at the bottom to keep the catalyst bed in the center of the furnace's isothermal zone. Typically, 1.0 g of catalyst was sized to 20/40 sieve mesh or cut to 1:1 l/d and dispersed with quartz chips (20/40 mesh) to a volume of 5.5 cc. When loaded, the catalyst bed measured about 12.5 cm in height. The reactor was topped off with the same size quartz or larger size up to 14 mesh. The reactor was installed in a furnace with the catalyst bed in the middle of the furnace at a pre-marked isothermal zone. The reactor was then pressure and leak tested at approx. 300 psig.

The catalyst was pre-conditioned in situ; heated to 375° C. to 460° C. with $H_2$ flow at 100 cc/min and held for 2 hours.

A 500 cc ISCO syringe pump was used to introduce the hydroalkylated feed described above to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 100 psig. GC analyses were taken to verify feed composition. The feed was then pumped through the catalyst bed held at a reaction temperature of 375° C. to 460° C. at a WHSV of 2 and a pressure of 100 psig. The products exiting the reactor flowed through heated lines routed to two collection pots in series. The non-condensable gas products were routed to an on line HP 5890 GC. The first pot was heated to 60° C. and the second pot cooled with chilled coolant to about 10° C. Material balances were taken at 12 and 24 hour intervals. Samples were taken and diluted with 50% ethanol for analysis. This product was distilled (see example 30E below) to remove the unreacted toluene and the methylcyclohexane that was produced.

Example 30E: Distillation

Toluene and methyl cyclohexane were removed from the product of example 30E using a rotovap setup at 70° C. under vacuum. For dimethyl biphenyl distillation the following setup was used: The crude dimethylbiphenyl product was charged into a 3-necked-5-liter round bottom distillation flask attached to a 3' oldershaw column (21 theoretical trays). The round bottom was fitted with a thermometer, nitrogen sparger, chilled water condenser and the column fed a multiple receiving adapter with and a dry ice/isopropanol cooled trap. The round bottom flask was heated at 200° C. with a reflux ratio of 10:1. Approximately 50 gram distillation cuts were collected and analyzed by GC. The fractions which were collected at 120-130° C. at a vacuum of 0.5-1 mmHg were combined after they were analyzed by GC. The combined sample was the re-analyzed by GC. The composition of this sample was: 2,3'DMBP-0.70%; 2,4'DMBP-2.54%; 3,3'DMBP-19.74%; 3,4'DMBP-52.78%; 4,4'DMBP-24.23%. This sample was then oxidized according to the procedure in example 30F below.

Example 30F: Oxidation

Oxidation of the purified dehydrogenated feed produced in example 30E is described below: Oxidation was done batchwise and the batches combined before carrying out the monoacid isolation and purification. A 300 ml Parr reactor was charged with 115.6 grams of feed, 1.45 grams of cobalt (II) chloride hexahydrate, 1.41 grams of didodecyl dimethylammonium bromide and 1.25 grams of t-butylhydroperoxide. The reactor was sealed and pressurized to 500 psi with air. The air flow rate was set at 750 cc/min. The reactor was heated to 150° C. with a stir rate of 1200 rpm. After 6 hours reaction time the reactor was cooled to room temperature, then depressurized. The reactor was disassembled and the contents removed.

Example 30G: Mono-Acid Isolation

Five oxidation runs (722.1 grams) were combined and dissolved into 2500 ml of methanol. The mixture was stirred and heated to reflux for one hour. The mixture was cooled to room temperature and the solids were allowed to settle overnight. The above mixture was filtered to remove most of the di-acid. The methanol soluble portion was placed on a Rotovap to remove the methanol. The residue was added to 2000 ml of water and cooled using an ice water bath. 200 grams of a 50% NaOH solution was diluted with 200 ml of water. The NaOH solution was slowly added to the cooled water mixture maintaining the temperature below 20° C. The mixture was transferred to a separatory funnel and extracted with toluene. The toluene was separated from the aqueous phase. The aqueous phase was cooled using an ice water bath. 100 ml of concentrated HCl, diluted with 100 ml water, was slowly added to precipitate the mono-acid. The above mixture was filtered and the solids were washed three times with water. The solids were then placed in a vacuum oven at 60° C. under house vacuum to dry. 375 grams were recovered.

Example 30H: Esterification of Monoacid

To a 2 liter round bottom flask fitted with a thermometer, Dean-Stark trap, condenser, air stirring and heating mantle was added 254.2 grams (1.2 moles) of the isolated monoacid described above, 570.76 grams (3.6 moles) Exxal™ C10 alcohol and 100 ml xylenes. The mixture was slowly heated and water was collected in the Dean-Stark trap. The final temperature attained after 23 hrs was 194° C. and the total water collected was 87.4 grams. The mixture was cooled to room temperature. The mixture was transferred to a distillation flask where the xylenes and unreacted alcohol were removed. The maximum temperature was 212° C. at 0.2 mmHg 417.0 grams of residue remained for distillation.

Example 30I: Purification (Distillation) of Monoester

The esterified mixture from example 3H was placed in a Kugelrohr and the monoester was distilled at greater than 200° C. at 0.05 mmHg. The distilled monoester was further purified by column chromatography.
General Procedure for Column Chromatography:
Preparation of Columns:
Silica gel (70-90 um, 60 A) is dispensed from a 25 kilogram drum using a large plastic scoop. The silica is transferred from the drum to a large (4 L) beaker located inside the fume hood. The silica is then slurried in several liters of hexanes, using manual stirring. Once flow is established, the silica slurry is poured into a 3000 mL, 150M fritted, glass funnel, which sits atop a 4 L vacuum flask. Once the silica has settled, vacuum is applied on the flask, allowing the silica gel to pack. The resulting silica bed is 5.5 inches wide and approximately 6 inches in height. Resulting fractions were analyzed by Thin Layer Chromatography (TLC) in 5% ethyl acetate in hexanes.
After the distillation in example 30I above, samples were run in batches of 100-200 g each. With the flask is under vacuum, 100 g of impure ester, dissolved in minimum amount of hexanes, is added to the packed silica gel. Product is then eluted by washing the silica bed with 3.8 liters of 5% ethyl acetate in hexanes (Fraction 1), followed by 1 liter of 5% ethyl acetate in hexanes (Fraction 2).
Analysis of fractions by TLC indicates purified ester with a faint trace of impurity.
Fractions were combined and concentrated down on a rotary evaporator, under vacuum, at 50° C. before final drying overnight under pump vacuum. Yield, after vacuum drying, is ~85% of mostly colorless, but slightly cloudy, viscous liquid.
After column purification the mixture was front end stripped using the Kugelrohr. The stripped monoester was bubbled with nitrogen to remove cloudiness. GC analysis of the final product was consistent with formation of a mixture of OXO-$C_{10}$ monoester isomers (99%).

This invention also relates to:

1. Compounds of the formula

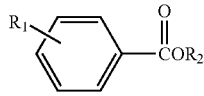

wherein $R_1$ is a saturated or unsaturated cyclic hydrocarbon optionally substituted with an alkyl and/or an OXO-ester, and $R_2$ is a hydrocarbon residue of a $C_4$ to $C_{14}$ OXO-alcohol.

2. The compounds of clause 1, wherein $R_1$ is located at the ortho-, meta- or para-position.

3. The compounds of clause 1, wherein $R_1$ is phenyl located at the para-position.

4. The compounds of clause 1, wherein $R_1$ is an alkyl and/or an OXO-ester-substituted phenyl at the ortho-, meta-, or para-position.

5. The compounds of clause 1, wherein $R_1$ is an alkyl and/or an OXO-ester-substituted cyclohexyl at the ortho-, meta-, or para-position.

6. The compounds of any of the preceding clauses, wherein $R_2$ is the hydrocarbon residue of a $C_5$ to $C_{10}$ OXO-alcohol averaging from 0.2 to 5.0 branches per residue.

7. The compounds of any of the preceding clauses, wherein the hydrocarbon residue averages from 0.05 to 0.4 branches per residue at the alcoholic beta carbon.

8. The compounds of any of the preceding clauses, wherein the hydrocarbon residue averages at least 1.3 to 5.0 methyl branches per residue.

9. The compounds of any of the preceding clauses, wherein the hydrocarbon residue averages from 0.35 to 1.5 pendant methyl branches per residue.

10. A process for making compounds of the formula:

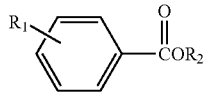

wherein $R_1$ is a cyclic hydrocarbon optionally substituted with an alkyl and/or an OXO-ester, and $R_2$ is a hydrocarbon residue of a $C_4$ to $C_{14}$ OXO-alcohol, comprising the steps of: reacting benzene or alkylated benzene under conditions appropriate to form alkylated biphenyl; optionally alkylating biphenyl to form said alkylated biphenyl; oxidizing the alkyl group(s) on said alkylated biphenyl to form at least one acid group; and reacting said acid group(s) with an OXO-alcohol under esterification conditions to form said compounds.

11. The process of clause 10, wherein said reacting step is conducted with benzene, and said optional alkylating step is conducted with an alcohol.

12. The process of clauses 10-11, wherein said alcohol is methanol and said alkylating step is conducted in the presence of an acid catalyst.

13. The process of clause 10, wherein said reacting step is conducted with benzene, further comprising the steps of: hydroalkylating benzene by reacting benzene in the presence of $H_2$ to hydrogenate one mole of said benzene to form cyclohexene, alkylating benzene with said cyclohexene to form cyclohexylbenzene; dehydrogenating said cyclohexyl-benzene to form biphenyl; and alkylating one or both aromatic moieties of said biphenyl to form said alkylated biphenyl.

14. The process of clause 13, wherein said hydroalkylating step is conducted in the presence of a hydrogenation catalyst, said alkylating step is conducted with an alkylation catalyst, and said dehydrogenating step is conducted with a dehydrogenation catalyst.

15. The process of clause 14, wherein said hydrogenation catalyst is selected from the group consisting of platinum, palladium, ruthenium, nickel, zinc, tin, cobalt, or a combination of these metals, with palladium being particularly advantageous; said alkylation catalyst is selected from the group consisting of Zeolite, mixed metal oxides and said dehydrogenation catalyst is selected from the group consisting of platinum, pladium, Ru, Rh, nickel, zinc, tin, cobalt and combinations thereof.

16. The process of clause 10, wherein said reacting step is conducted with benzene in the presence of oxygen and an oxidative coupling catalyst, forming biphenyl, further comprising the step of: alkylating one or both aromatic moieties of said biphenyl to form said alkylated biphenyl.

17. The process of clause 16, wherein said alkylating step is conducted with an alkylation catalyst.

18. The process of clause 10, wherein the reacting step is conducted with toluene, further comprising the steps of: reacting toluene in the presence of $H_2$ and a hydrogenation catalyst to form methyl cyclohexene; reacting said methyl cyclohexene with toluene in the presence of an alkylation catalyst to form methyl cyclohexyl toluene; and dehydrogenating said methyl cyclohexyl toluene in the presence of a dehydrogenation catalyst to form the alkylated biphenyl, which is dimethyl-biphenyl.

19. A polymer composition comprising a thermoplastic polymer and at least one plasticizer of the formula:

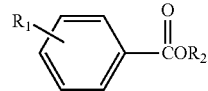

wherein $R_1$ is a saturated and unsaturated cyclic hydrocarbon optionally substituted with an alkyl and/or an OXO-ester, and $R_2$ is a hydrocarbon residue of a $C_4$ to $C_{14}$ OXO-alcohol.

20. A polymer composition comprising a thermoplastic polymer and at least one compound of any of claims 1 to 9 or the product of the process of any of claims 10 to 18.

21. The polymer composition of clause 19 or 20, wherein the thermoplastic polymer is selected from the group consisting of vinyl chloride resins, polyesters, polyurethanes, ethylene-vinyl acetate copolymer, rubbers, poly(meth)acrylics and combinations thereof.

22. The composition of clause 1 wherein $R^1$ is tolyl and $R^1$ is a $C_9$ or $C_{10}$ hydrocarbyl.

23. The composition of clauses 1 to 9, or 22 wherein the compound comprises analogs that have been fully or partially hydrogenated.

24. The composition of clause 1 or 23 wherein $R^1$ is a saturated or unsaturated cyclic hydrocarbon substituted with an OXO-ester.

25. The polymer composition of clause 19, 20 or 21 wherein the thermoplastic polymer is polyvinyl chloride.

26. A mixture comprising at least two compounds of the formula:

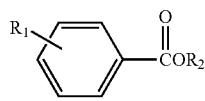

wherein in the first compound, $R_1$ is a saturated cyclic hydrocarbon optionally substituted with an alkyl and/or an OXO-ester, and $R_2$ is a $C_4$ to $C_{14}$ hydrocarbyl, preferably a hydrocarbon residue of a $C_4$ to $C_{14}$ OXO-alcohol; and in the second compound $R_1$ is an unsaturated cyclic hydrocarbon optionally substituted with an alkyl and/or an OXO-ester, and $R_2$ is a $C_4$ to $C_{14}$ hydrocarbyl, preferably a hydrocarbon residue of a $C_4$ to $C_{14}$ OXO-alcohol.

27. The mixture of clause 26 where each $R^1$ is a $C_6$ ring optionally substituted with an alkyl and/or an OXO-ester.

28. A mixture comprising at least two compounds of the formula:

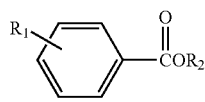

wherein each $R_1$ is, independently, a saturated or unsaturated cyclic hydrocarbon optionally substituted with an alkyl and/or an OXO-ester, and each $R_2$ is, independently, a $C_4$ to $C_{14}$ hydrocarbyl, preferably a hydrocarbon residue of a $C_4$ to $C_{14}$ OXO-alcohol.

29. A wire and cable coating formulation comprising: i) 100 parts by weight PVC; (ii) 20 to 80 parts of the compounds of any of clauses 1-9, 22, 24, 26, 27 or 28; (iii) a filler; and (iv) a stabilizer.

30. A cable insulation formulation according to clause 29 wherein the filler is present at from 1 to 100 parts by weight per 100 parts of the PVC and the stabilizer is present at from 5 to 15 parts by weight per 100 parts of the PVC.

31. A cable filling compound formulation according to clause 29 wherein the filler is present at from 1 to 600 parts by weight per 100 parts of the PVC and the stabilizer is present at from 5 to 15 parts by weight per 100 parts of the PVC.

32. A wire or cable coated with a composition or formulation of clause 19-21, 25, 29 or 30.

33. A composition according to clause 19-21, wherein the composition comprises the plasticizer of claim 1 in an amount of from 5 to 90% by mass per 100 parts by mass of the polymer.

34. A composition according to clause 19-21 wherein the composition comprises additional plasticizer selected from the group consisting of a dialkyl phthalate, a trialkyl trimellite, a dialkyl adipate, a dialkyl terephthalate, a dialkyl cyclohexanedicarboxylate, a benzoic ester, a glycol ester, an alkylsulphonic ester, a glycerol ester, an isosorbide ester, a citric ester, an alkylpyrrolidone, and an epoxidized oil.

35. A composition according to clause 19-21, further comprising: a PVC suspension, a PVC microsuspension, a PVC emulsion, or a combination thereof.

36. A composition according to clause 19-21, further comprising: an additive selected from the group consisting of a filler, a pigment, a matting agent, a heat stabilizer, an antioxidant, a UV stabilizer, a flame retardant, a viscosity regulator, a solvent, a deaerating agent, an adhesion promoter, a process aid, and a lubricant.

37. A floor covering, comprising: the composition according to clause 35.

38. A wallpaper, comprising: the composition according to clause 35.

39. A tarpaulin, comprising the composition according to clause 35.

40. A coated textile, comprising: the composition according to clause 35.

41. A wall covering, comprising: the composition according to clause 35.

42. A film, comprising: the composition according to clause 35 wherein the film is a roofing sheet, a tarpaulin, an advertising banner, synthetic leather, packaging film, a medical article, a toy, a seal, or an automobile interior article.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications (including priority documents), test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a™ symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

The invention claimed is:

1. A mixture comprising at least two compounds represented by the formula:

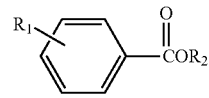

wherein $R_1$ is a saturated or unsaturated cyclic hydrocarbon substituted with an OXO-ester, and $R_2$ is a $C_4$ to $C_{14}$ hydrocarbyl, wherein in the first compound, $R_1$ is a saturated cyclic hydrocarbon substituted with OXO-ester, and in the second compound $R_1$ is an unsaturated cyclic hydrocarbon substituted with an OXO-ester.

2. The mixture of claim 1, wherein in the first and/or second compound $R_1$ is located at the ortho-, meta- or para-position.

3. The mixture of claim 2, wherein in the second compound $R_1$ is a phenyl group located at the para-position where the phenyl is substituted with an OXO-ester at the ortho-, meta-, or para-position.

4. The mixture of claim 1, wherein in the first and/or second compound $R_2$ is not linear.

5. The mixture of claim 1, wherein in the first and/or second compound $R_2$ is branched.

6. The mixture of claim 1 where each $R_1$ is a $C_6$ ring optionally substituted with an OXO-ester.

7. A process for making a mixture comprising at least two compounds of the formula:

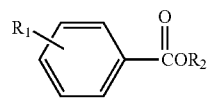

wherein $R_1$ is a cyclic hydrocarbon substituted with an OXO-ester, and $R_2$ is a $C_4$ to $C_{14}$ alkyl group, wherein in the first compound, $R_1$ is a saturated cyclic hydrocarbon substituted with OXO-ester, and in the second compound $R_1$ is an unsaturated cyclic hydrocarbon substituted with an OXO-ester, the process comprising the steps of:

reacting benzene or alkylated benzene under conditions appropriate to form alkylated biphenyl;

optionally alkylating biphenyl to form said alkylated biphenyl;

oxidizing the alkyl group(s) on said alkylated biphenyl to form acid groups; and reacting said acid groups with an OXO-alcohol under esterification conditions to form said compounds, wherein after reacting said acid groups with an OXO-alcohol under esterification conditions, the reaction product is contacted with a basic solution.

* * * * *